(12) United States Patent
Chowdhury

(10) Patent No.: US 11,396,527 B2
(45) Date of Patent: Jul. 26, 2022

(54) DUAL MASS SPECTROMETRY-CLEAVABLE CROSSLINKING REAGENTS FOR PROTEIN-PROTEIN INTERACTIONS

(71) Applicant: Board of Regents, The University of Texas System, Austin, TX (US)

(72) Inventor: Saiful Mahmud Chowdhury, Bedford, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/923,811

(22) Filed: Jul. 8, 2020

(65) Prior Publication Data

US 2020/0354403 A1    Nov. 12, 2020

Related U.S. Application Data

(62) Division of application No. 16/307,375, filed as application No. PCT/US2017/035987 on Jun. 5, 2017, now Pat. No. 10,752,655.

(60) Provisional application No. 62/345,844, filed on Jun. 5, 2016.

(51) Int. Cl.
| | |
|---|---|
| *C07K 7/06* | (2006.01) |
| *C07K 5/103* | (2006.01) |
| *C07K 5/093* | (2006.01) |
| *G01N 33/68* | (2006.01) |

(52) U.S. Cl.
CPC .......... *C07K 5/1008* (2013.01); *C07K 5/0819* (2013.01); *C07K 7/06* (2013.01); *G01N 33/6848* (2013.01)

(58) Field of Classification Search
CPC ...... C07K 5/1008; C07K 5/0819; C07K 7/06; G01N 33/6848
See application file for complete search history.

(56) References Cited

U.S. PATENT DOCUMENTS

| | | | | |
|---|---|---|---|---|
| 2008/0090298 | A1* | 4/2008 | Apffel | G01N 30/7233 436/86 |
| 2011/0070596 | A1* | 3/2011 | Wood | G01N 33/6848 435/7.8 |

OTHER PUBLICATIONS

Chowdhury, et al., "Identification of cross-linked peptides after click-based enrichment using sequential collision-induced dissociation and electron transfer dissociation tandem mass spectrometry", Anal Chem., 81:5524-32 (2009).

Greber, et al., "Ribosome. The complete structure of the 55S mammalian mitochondrial ribosome", Science, 348:303 (2015).

Greber, et al., "The complete structure of the large subunit of the mammalian mitochondrial ribosome", Nature, 515:283-6 (2014).

Gutierrez, et al., "Developing an Acidic Residue Reactive and Sulfoxide-Containing MS-Cleavable Homobifunctional Cross-Linker for Probing Protein-Protein Interactions", Anal Chem, 88(16): 8315-22 (2016).

International Search Report PCT/US17/35987 dated Aug. 24, 2017.

Kimble, et al., "Overview of affinity tags for protein purification", Curr Protoc Protein Sci., 73:Unit 9.9. doi: 10.1002/0471140864 (2013).

Lauber, et al., "Dynamics of ribosomal protein S1 on a bacterial ribosome with cross-linking and mass spectrometry", Mol Cell Proteomics, 11(12):1965-76 (2012).

Nesvizhskii, et al., "A statistical model for identifying proteins by tandem mass spectrometry", Anal. Chem, 75(17):4646-58 (2003).

Petrotchenko, et al., "An isotopically coded CID-cleavable biotinylated cross-linker for structural proteomics", MCP, 10:M110 001420 (2011).

Soderblom, et al., "Collision-induced dissociative chemical cross-linking reagents and methodology: applications to protein structural characterization using tandem mass spectrometry analysis", Anal Chem. 78:8059-68 (2006).

Tan, et al., "Decoding gripping force based on local field potentials recorded from subthalamic nucleus in humans", eLife, 5 pii: e19089. doi: 10.7554/eLife.19089 (2016).

Tang, et al., "A new cross-linking strategy: protein interaction reporter (PIR) technology for protein-protein interaction studies", Mol. Biosyst., 6(6):939-47 (2010).

Tang, et al., "Mass spectrometry identifiable cross-linking strategy for studying protein-protein interactions", Anal Chem., 77:311-8 2005).

Vasicek, et al., "Mapping Protein Surface Accessibility via an Electron Transfer Dissociation Selectively Cleavable Hydrazone Probe", Molecular & Cellular Poteomics, 11:1-10 (2012).

Yu, et al., "Characterization of Dynamic UbR-Proteasome Subcomplexes by In vivo Cross-linking (X) Assisted Bimolecular Tandem Affinity Purification (XBAP) and Label-free Quantitation", Mol Cell Proteomics, 15(7):2279-92 (2016).

* cited by examiner

*Primary Examiner* — Timothy R Rozof
(74) *Attorney, Agent, or Firm* — Pabst Patent Group LLP

(57) ABSTRACT

Described are dual mass-spectrometry-cleavable cross-linkers that can be cleaved selectively using two differential tandem mass-spectrometric techniques such as collision induced dissociation (CID) or electron transfer dissociation (ETD), i.e., a dual cleavable crosslinking technology (DUCCT) cross-linker. When used to cross-link a macromolecule, such as a peptide, MS/MS fragmentation produces two signature complementary mass spectra of same cross-linked peptides, the analysis of which gives rise to high confidence in characterizing the structures of the cross-linked macromolecules as well as sites of interactions. Also described, are methods of making and using DUCCT cross-linkers.

19 Claims, 22 Drawing Sheets
Specification includes a Sequence Listing.

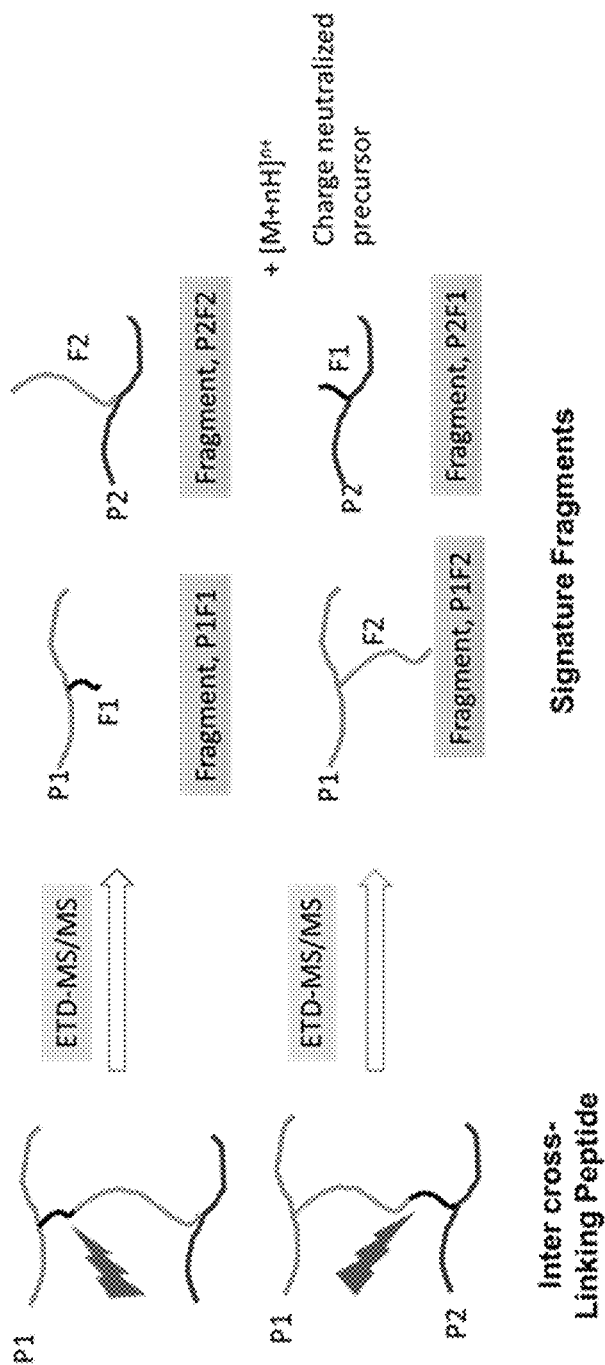
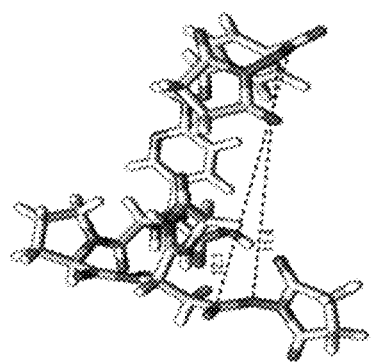
FIG. 2C
FIG. 3
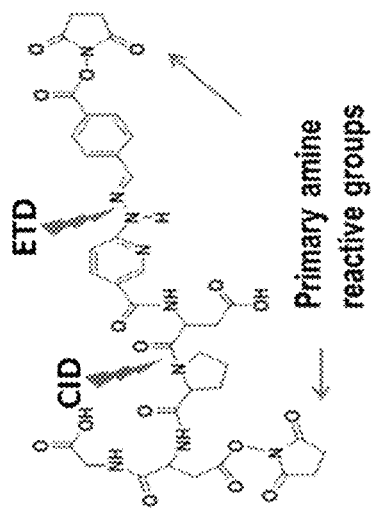

1. Bio-LPS
2. BioLPS-BiotinBS3
3. BioLPS-DUCCT

DUAL MASS SPECTROMETRY-CLEAVABLE CROSSLINKING REAGENTS FOR PROTEIN-PROTEIN INTERACTIONS

CROSS REFERENCE TO RELATED APPLICATIONS

This application is a divisional of U.S. application Ser. No. 16/307,375 filed Dec. 5, 2018, which is a National Phase application under 35 U.S.C. § 371 of International Application No. PCT/US2017/035987, filed Jun. 5, 2017, which claims benefit of and priority to U.S. Provisional Application No. 62/345,844 filed Jun. 5, 2016, and where permissible are hereby incorporated by reference in their entirety.

GOVERNMENT GRANT

This invention was made with government support under Grant No. 1US5GM113216-01 awarded by the National Institutes of Health. The government has certain rights in the invention.

Reference to Sequence Listing

The Sequence Listing submitted Aug. 26, 2019 as a text file named "UTSB_16_45_371_ST25.txt" created on Aug. 26, 2016, and having a size of 4,405 bytes is hereby incorporated by reference.

FIELD OF THE INVENTION

The present invention relates generally to the field of cross-linking agents and, more specifically, compositions which can be cleaved selectively using two differential tandem mass-spectrometric fragmentations such as collision induced dissociation (CID) or electron transfer dissociation (ETD) to produce two signature mass spectra of same cross-linked peptides, thereby producing high confidence in identifying sites of interactions.

BACKGROUND

Proteins form stable and dynamic multi-subunit complexes under different physiological conditions to maintain cell viability and normal cell homeostasis. Detailed knowledge of protein interactions and protein complex structures is fundamental to understanding how individual proteins function within a complex and how the complex functions as a whole. However, structural elucidation of large multi-subunit protein complexes has been difficult due to lack of technologies which can effectively handle their dynamic and heterogeneous nature. Traditional biophysical methods such as nuclear magnetic resonance (NMR) analysis and X-ray crystallography can yield detailed information on protein structures; however, NMR spectroscopy requires large quantities of pure protein in a specific solvent while X-ray crystallography is often limited by the crystallization process.

Current biochemical methods are not very efficient to analyze system-level or large-scale protein interaction networks. Most of the studies utilize a technique called "co-immunoprecipitation," where a protein is isolated along with its interacting partners (protein complexes) by using an antibody or by incorporating an affinity group in the protein which can be used as a hook to selectively purify that protein. This method is applicable for very strong and stable interactions, but most of the cellular interactions are very transient and weak, and during the purification process these interactions get lost completely. Besides, this identification is very qualitative and does not put emphasis on the protein-to-protein interaction domain.

One chemistry-based fixation method combined with mass spectrometry technology utilizes a crosslinker to stabilize proteins with its interaction partners (protein complexes) by using certain side chains of proteins)) before performing cell lysis. Crosslinkers can fix the nearby proteins or protein complexes by chemical reactions and hold them tightly so they will not detach after cell lysis and will not be affected by the subsequent strict purification conditions. In addition, a crosslinker reacts within a limited distance; hence, protein reactive sites can be measured by calculating the distances of the reactive sites. This method can identify large-scale protein interactions and it can identify protein structures in their native biological conditions.

Although cross-linking coupled with mass spectrometry (MS) has been presented as a feasible strategy for structural elucidation of large multi-subunit protein complexes, this method has proven challenging due to technical difficulties in unambiguous identification of cross-linked peptides and determination of cross-linked sites by MS analysis. The universal use of this technology is hindered due to several bottlenecks. Previously disclosed crosslinking strategies generate an enormous amount of mass spectrometry data which is extremely difficult to analyze by routine software tools. Finding these interactions in large datasets is akin to finding a needle in a haystack. Examples of known cross-linking strategies include selective enrichment using click chemistry with alkyne-tagged (Chowdhury, et al., *Anal Chem.*, 81:5524-5532 (2009)); affinity enrichment combined with isotopic coding and CID cleavage (Petrotchenko, et al., *MCP*, 10:M110 001420 (2011); MS-cleavable reagents (Soderblom, et al., *Anal Chem.* 78:8059-8068 (2006)); and Tang, et al., *Anal Chem.*, 77:311-318 2005)); crosslinking using the amine-reactive disuccinimidyl suberate (DSS) (Greber, et al., *Nature*, 515:283-286 (2014)) and Greber, et al., *Science*, 348:303 (2015)); lysine-targeted enrichable cross-linker containing a biotin tag (Tan, et al., *eLife*, 5 (2016)); in vivo cross-linking (X) assisted bimolecular tandem affinity purification strategy (Yu, *Molecular & Cellular Proteomics*, 15(7):2279-92 (2016)); and amidinating protein cross-linker, DEST (diethyl suberthioimidate) (Lauber, et al., *Molecular & Cellular Proteomics*, 11(12):1965-76 (2012)) and acidic residue reactive cleavable cross-linker (*Anal Chem.* 2016 Aug. 16; 88(16): 8315-8322).

There remains a need to make crosslinking technology very amenable for analyzing large-scale protein interactions, through the design of more effective chemical crosslinkers with innovative features, which will help reduce the complexity of mass-spectrometry data from large-scale protein interactions, and easy to analyze software tools.

It is an object of the present invention to provide chemical crosslinkers which reduce the complexity of mass-spectrometry data.

It is still an object of the present invention to provide a method of making chemical crosslinkers which reduce the complexity of mass-spectrometry data.

It is also an object of the present invention to provide a method for identifying crosslinked peptides with improved fidelity.

SUMMARY OF THE INVENTION

The present invention provides dual mass spectrometry-cleavable cross-linkers which can be fragmented by two differential tandem mass spectrometry (MS/MS) techniques (herein, dual cleavable crosslinking technology (DUCCT)). Two differential tandem mass-spectrometric fragmentations produce different signatures in the mass spectra for the same cross-linked macromolecule (e.g. peptides). These two complimentary fragmentation signatures identify the cross-linked peptides with high confidence. Further MS/MS of cross-linked macromolecules (e.g. peptides), produces additional confidence in identification.

Accordingly, crosslinker compositions are provided which include at least two reactive groups separated by a spacer or linker region that in turn includes at least two different cleavable bonds. In some embodiments, the two reactive groups are the same. In other embodiments, the two reactive groups are different. In a preferred embodiment, the distance between the reactive groups in the disclosed cross-linkers is between 11.0 Å and 12 Å, inclusive. A preferred reactive group is N-hydroxy succinimide (NHS), for conjugation of amino acids containing an amine in their side chains, such as lysines. In a particularly preferred embodiment, the crosslinker includes two NHS groups. In one preferred embodiment, the cleavable bonds are gas phase cleavable. In this embodiment, one of the bonds is preferably a Pro-Asp bond (DP) which can be cleaved by low energy CID. The second bond, preferably a nitrogen-nitrogen hydrazone bond is added, which provides a site for ETD cleavage. Both cleavable bonds are sandwiched in between the two NHS ester reactive groups which finally constitute a lysine reactive dual mass spectrometry cleavable cross-linker.

Dual mass spectrometry cleavable crosslinker compositions which include an enrichment reagent are provided. The enrichment reagent is preferably is one member of a pair of molecules with bind to each other with specificity (for example an affinity tag) such as biotin. These compositions allow enrichment of the cross-linked peptides from a large-scale experiment using the binding partner of the enrichment (used as a capture agent), used as a: "fishing hook" to capture the crosslinker-enrichment reagent complex. The capture reagent can be immobilized in a purification system, for example biotin-avidin affinity chromatography. The enrichment reagent is attached to the crosslinker, directly or indirectly, via a cleavable bond, preferably, a photo-cleavable bond. Both CID and ETD cleavage sites are incorporated into the crosslinker using the same chemistry for the dual mass spectrometry cleavable crosslinker disclosed above, i.e., the crosslinker that does not include an affinity group. The cleavable bond that is involved in attaching enrichment reagent (e.g. biotin) to the crosslinker, can be cleaved after exposure to UV-light (photo-cleavage) in order to release the cross-linked peptides from the capture agent (for example, avidin beads). Subsequent CID and ETD MS/MS generate signature mass spectra for identification of cross-linked peptides.

Also disclosed is a method of making crosslinker compositions which include at least two reactive groups separated by a spacer or linker region that in turn includes at least two different cleavable bonds. The method involves reacting a first pair of reagents (for example two amino acids, such as aspartate and proline) to form a first product (for example a dipeptide), wherein one of the reagents contains a chemical moiety that can be further reacted with a reactive group; reacting the first product with another reagent (for example another amino acid such as aspartate) to form a second product that contains a first cleavage site; reacting the second product with a reagent (such as Fmoc-6-hydrazinonicotinic acid) to form a third product; and reacting the third product with another reagent (for example a bivalent reagent such as 4-formylbenzoic acid) to form a fourth product that now contains the first cleavage site and a second cleavage site, wherein the reagent contains a chemical moiety that can be further reacted with a reactive group. The chemical moieties that can be further reacted with reactive groups are reacted with reactive groups (such as N-hydroxysuccinimide) to add these groups to the cross-linker. The method in some embodiments includes adding an enrichment reagent (such as biotin) to the cross-linker directly or indirectly at any of the reagents incorporated into the cross-linker.

Also disclosed is a method for identifying crosslinked macromolecules (e.g. peptides) with improved accuracy. The method includes the steps of contacting a cross-linker containing at least two cleavage sites that are differentially cleaved by at least two different mass spectrometric techniques, optionally containing an enrichment reagent, with a macromolecule, under conditions in which two or more reactive groups in the cross-linker react with reactive groups in the macromolecule to form a cross-linked macromolecule; optionally degrading the cross-linked macromolecule, enzymatically (using an enzyme such as trypsin), chemically, hydrolytically, or a combination thereof, to form a first reaction mixture; optionally purifying the reaction mixture optionally via an affinity column to obtain a second reaction mixture; performing tandem mass spectrometry with the first reaction mixture or the second reaction mixture, using two different mass spectrometric fragmentation techniques that differentially cleave at least two of the cleavage sites; and analyzing the mass spectra from the two different mass spectrometric fragmentation techniques to obtain insights about the structure of the macromolecule.

The technique can be applied to characterize protein structures in cells as well as protein-protein complexes in cell signaling cascades and understanding these complexes in diseased or normal cells can help to find target biomarkers and potential therapeutics for several inflammatory disease including cancers.

Details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears.

FIGS. 2A-2C show a scheme to identify inter crosslinked peptide and dead-end peptide by CID and ETD tandem mass spectrometry.

FIG. 3 shows a CID and ETD MS-cleavable crosslinker with spacer chain length calculated showing the CID and EDT cleavable sites.

DESCRIPTION OF ILLUSTRATIVE EMBODIMENTS

I. Definitions

Figure 1A:
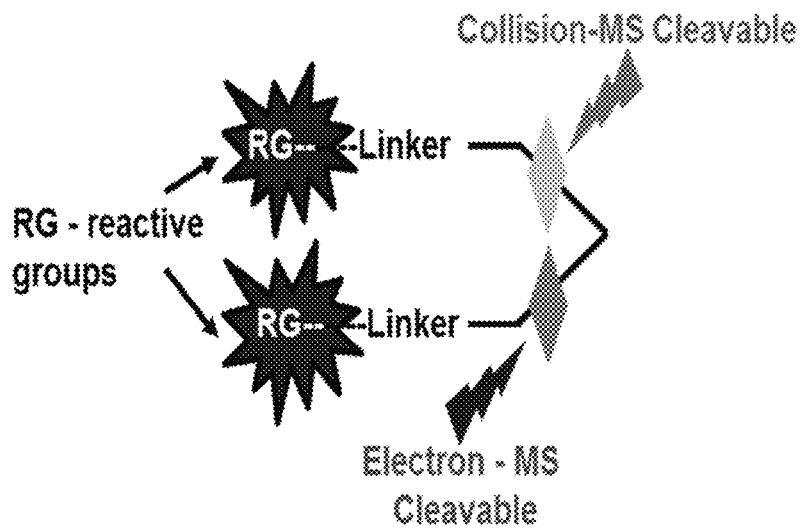
FIG. 1A illustrates the design of a dual cleavable cross-linking technology (DUCCT).

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

The terms "crosslinker" and "cross-linker" are used interchangeably, and refer to a molecule, preferably an organic molecule, containing two or more reactive groups that are separated by a spacer or linker region. Preferably, all the atoms in the spacer or linker region are involved in covalent bond formation. A cross-linker described herein may be referred to as "multivalent cross-linkers," "multivalent cross-linker" or simply as "cross-linker."

"Multivalent," as relates to a cross-linker, refers to a cross-linker with two or more reactive groups. Examples of multivalent cross-linkers include bivalent, trivalent, and tetravalent crosslinkers, denoting cross-linkers with two, three, and four reactive groups, respectively.

"Homo-functional," as relates to a multivalent cross-linker, refers to a multivalent cross-linker in which all the reactive groups have the same chemical constituents. As an example, all the reactive groups in the multi-valent cross-linker can be N-hydroxysuccinimide ester.

"Hetero-functional," as relates to a multivalent cross-linker, refers to a multivalent crosslinker in which at least two of its reactive groups are different. As an example, one reactive group can be N-hydroxysuccinimide ester and another reactive group can be isocyanate.

"Cleavage site" refers to a bond or group of atoms containing a bond that can be cleaved by a fragmentation technique used in a mass spectrometer. As an example, a cleavage site can be an amide bond, such as between proline and aspartate, or the nitrogen-nitrogen bond in or hydrazone "Affinity group," as used herein, refers to a chemical moiety, or an affinity molecule that can be included in a cross-linker, which enhances the detection and/or isolation of cross-linked products (e.g. macromolecules) in a reaction mixture by increasing the sensitivity of the detection instrument to the cross-linked product, enriching the reaction mixture with the cross-linked product, or both. The chemical moiety and molecule are used for purification purposes. For instance, during purification, the chemical moiety in the cross-linker forms a covalent bond with another chemical moiety immobilized in a purification system (e.g. column chromatography, or bead), thereby facilitating the isolation of the cross-linked product. The chemical moiety can be a reactive group such as alkyne, azide, and glycidyl. The affinity molecule functions similarly to the chemical moiety, but differs in that it attaches to another molecule immobilized in a purification system (e.g. affinity chromatography) via non-covalent bonds. Examples of affinity molecules include biotin, hemagglutinin, streptavidin, fusion protein, and antibody.

The term "amino acid," as used herein, refers to a molecule containing both an amino group and a carboxyl group. Amino acids include alpha-amino acids and beta-amino acids. In certain forms, an amino acid is an alpha amino acid. Amino acids can be natural or synthetic. Amino acids include, but are not limited to, the twenty standard or canonical amino acids: Alanine (Ala, A), Arginine (Arg, Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). Common non-standard or non-canonical amino acids include, but are not limited to, selenocysteine, pyrrolysine, and N-formylmethionine.

The term "natural amino acid," as used herein, refers to both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)).

The terms "synthetic amino acid," "non-natural amino acid," and "unnatural amino acid," are used interchangeably, and refer to an organic compound that has an amino group and a carboxyl group, and is not one of the D- and L-isomers of the 20 common naturally occurring amino acids found in peptides. Generally, it mimics the reactivity of a natural amino acid due to the presence of the amino and carboxyl groups. "Synthetic amino acid," "non-natural amino acid," or "unnatural amino acid" also refers to an amino acid that is not produced by an organism without genetic engineering. The synthetic amino acid as defined herein generally increases or enhances the properties of a peptide (e.g., selectivity, stability) when the synthetic amino acid is either substituted for a natural amino acid or incorporated into a peptide. Non-limiting examples include N-methyl glycine (sarcosine), 2,3-diaminobutyric acid, and 2,3-diamino propionic acid.

The term "macromolecule" refers to a molecule that has a molecular weight between 1 kDa and 500 kDa. Examples of macromolecules include peptides, proteins, glycoproteins, and nucleic acids.

"Substituted" refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Alkyl," as used herein, refers to the radical of saturated aliphatic groups, including straight-chain alkyl groups, branched-chain alkyl, cycloalkyl (alicyclic), alkyl substituted cycloalkyl groups, and cycloalkyl substituted alkyl. In preferred forms, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Alkyl includes methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like.

Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred forms, a substituent designated herein as alkyl is a lower alkyl.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —CON(R)$_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —CF3, —$CH_2$—$CF_3$, —$CCl_3$); —CN; —$NCOCOCH_2CH_2$, —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), haloalkyls, —CN and the like. Cycloalkyls can be substituted in the same manner.

"Heteroalkyl," as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

The terms "alkoxyl" or "alkoxy," "aroxy" or "aryloxy," generally describe compounds represented by the formula —OR$^v$, wherein R$^v$ includes, but is not limited to, substituted or unsubstituted alkyl, alkenyl, alkynyl, cycloalkyl, heterocyclyl, cycloalkenyl, heterocycloalkenyl, aryl, heteroaryl, arylalkyl, heteroalkyls, alkylaryl, alkylheteroaryl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The term alkoxy also includes cycloalkyl, heterocyclyl, cycloalkenyl, heterocycloalkenyl, and arylalkyl having an oxygen radical attached to at least one of the carbon atoms, as valency permits. A "lower alkoxy" group is an alkoxy group containing from one to six carbon atoms.

The term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "alkenyl" as used herein is a hydrocarbon group of from 2 to 24 carbon atoms and structural formula containing at least one carbon-carbon double bond. Asymmetric structures such as (AB)C═C(CD) are intended to include both the E and Z isomers. This may be presumed in structural formulae herein wherein an asymmetric alkene is present, or it may be explicitly indicated by the bond symbol C.

The term "alkynyl group" as used herein is a hydrocarbon group of 2 to 24 carbon atoms and a structural formula containing at least one carbon-carbon triple bond.

The term "aryl" as used herein is any $C_5$-$C_{26}$ carbon-based aromatic group, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, including, but not limited to, benzene, naphthalene, anthracene, phenanthrene, chrysene, pyrene, corannulene, coronene, etc. "Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/ or heterocycles. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as CF3, —CH$_2$—CF$_3$, —CCl$_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as CF3, —CH$_2$—CF$_3$, —CCl$_3$), —CN, aryl, heteroaryl, and combinations thereof.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aralkyl" as used herein is an aryl group having an alkyl, alkynyl, or alkenyl group as defined above attached to the aromatic group. An example of an aralkyl group is a benzyl group.

The term "hydroxyalkyl group" as used herein is an alkyl, alkenyl, alkynyl, aryl, aralkyl, cycloalkyl, halogenated alkyl, or heterocycloalkyl group described above that has at least one hydrogen atom substituted with a hydroxyl group.

The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

"Carbonyl," as used herein, is art-recognized and includes such moieties as can be represented by the general formula:

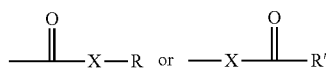

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R", or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or —(CH$_2$)$_m$—R"; R" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate'. Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, wherein one or more hydrogen atoms in R, R' or a group to which the moiety

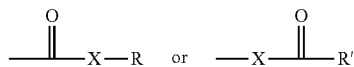

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "carboxyl" is as defined above for the formula

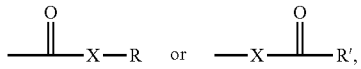

and is defined more specifically by the formula —$R^{iv}$COOH, wherein $R^{iv}$ is an alkyl, alkenyl, alkynyl, cycloalkyl, heterocyclyl, alkylaryl, arylalkyl, aryl, or heteroaryl. In preferred forms, a straight chain or branched chain alkyl, alkenyl, and alkynyl have 30 or fewer carbon atoms in its backbone (e.g., $C_1$-$C_{30}$ for straight chain alkyl, $C_3$-$C_{30}$ for branched chain alkyl, $C_2$-$C_{30}$ for straight chain alkenyl and alkynyl, $C_3$-$C_{30}$ for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure.

The term "substituted carboxyl" refers to a carboxyl, as defined above, wherein one or more hydrogen atoms in $R^{iv}$ are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenoxy" is art recognized, and refers to a compound of the formula —$OR^v$ wherein $R^v$ is (i.e., —O—$C_6H_5$). One of skill in the art recognizes that a phenoxy is a species of the aroxy genus.

The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, wherein aryl and heteroaryl are as defined herein.

The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenylthio" is art recognized, and refers to —S—$C_6H_5$, i.e., a phenyl group attached to a sulfur atom.

The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, wherein aryl and heteroaryl as defined herein.

The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "amide" or "amido" are used interchangeably, refer to both "unsubstituted amido" and "substituted amido" and are represented by the general formula:

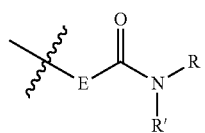

wherein, E is absent, or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of R and R' can be a carbonyl, e.g., R and R' together with the nitrogen do not form an imide. In preferred forms, R and R' each independently represent a hydrogen atom, substituted or unsubstituted alkyl, a substituted or unsubstituted alkenyl, or —(CH$_2$)$_m$—R'''. When E is oxygen, a carbamate is formed. The carbamate cannot be attached to another chemical species, such as to form an oxygen-oxygen bond, or other unstable bonds, as understood by one of ordinary skill in the art.

The term "sulfonyl" is represented by the formula

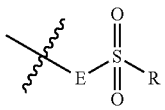

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or E and R taken together with the S atom to which they are attached complete a heterocycle having from 3 to 14 atoms in the ring structure; R'' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of E and R can be substituted or unsubstituted amine, to form a "sulfonamide" or "sulfonamido." The substituted or unsubstituted amine is as defined above.

The term "substituted sulfonyl" represents a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl.

The term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

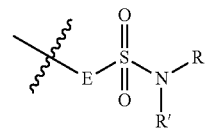

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of R and R' can be a carbonyl, e.g., R and R' together with the nitrogen do not form an imide.

The term "phosphonyl" is represented by the formula

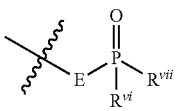

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein, independently of E, $R^{vi}$ and $R^{vii}$ are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', or R and R' taken together with the P atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "substituted phosphonyl" represents a phosphonyl in which E, $R^{vi}$ and $R^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phosphoryl" defines a phosphonyl in which E is absent, oxygen, alkoxy, aroxy, substituted alkoxy or substituted aroxy, as defined above, and independently of E, $R^{vi}$ and $R^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, $R^{vi}$ and $R^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof. When two or more heteroaryls are involved, the chemical moiety can be referred to as a "polyheteroaryl."

The term "substituted polyaryl" refers to a polyaryl in which one or more of the aryls, heteroaryls are substituted, with one or more substituents including, but not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof. When two or more heteroaryls are involved, the chemical moiety can be referred to as a "substituted polyheteroaryl."

The term "$C_3$-$C_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

The term "ether" as used herein is represented by the formula $AOA^1$, where A and $A^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "urethane" as used herein is represented by the formula —OC(O)NRR', where R and R' can be, independently, hydrogen, an alkyl, alkenyl, alkynyl, aryl, aralkyl, cycloalkyl, halogenated alkyl, or heterocycloalkyl group described above.

The term "silyl group" as used herein is represented by the formula —SiRR'R", where R, R', and R" can be, independently, hydrogen, an alkyl, alkenyl, alkynyl, aryl, aralkyl, cycloalkyl, halogenated alkyl, alkoxy, or heterocycloalkyl group described above.

The terms "hydroxyl" and "hydroxy" are used interchangeably and are represented by —OH.

The terms "thiol" and "sulfhydryl" are used interchangeably and are represented by —SH.

The term "oxo" refers to =O bonded to a carbon atom.

The terms "cyano" and "nitrile" are used interchangeably to refer to —CN.

The term "nitro" refers to —$NO_2$.

The term "phosphate" refers to —O—$PO_3$.

The term "azide" or "azido" are used interchangeably to refer to —$N_3$.

II. Compositions

Described herein, are multivalent cross-linkers containing at least two reactive groups and at least two sites (i.e., cleavage sites) within the spacer or linker region of the cross-linkers, which are differentially cleaved by two different tandem mass spectrometric techniques.

Preferably, at least two of the cleavage sites are located between at least two reactive groups. When these cross-linkers are used to cross-link a macromolecule, such as a peptide, for structural analysis using an analytical method, such as mass spectrometry, the described configuration of reactive groups and cleavage sites within the cross-linkers gives rise to two signature mass spectra of the same cross-linked macromolecule (e.g. a peptide). Analysis of the two complementary fragmentation signatures facilitates the determining the structural identity of the cross-linked macromolecule with high confidence. Further, tandem mass spectrometry of the cross-linked macromolecule, if necessary, leads to additional confidence in the characterization of the structures identified. Although these cross-linkers enhance determining the structural identities of cross-linked macromolecules, the isolation and/or identification of cross-linked products can be challenging due to the complexity of the reaction mixtures. Accordingly, in some forms, the cross-linkers contain an affinity group that facilitates the detection and/or isolation of cross-linked products present in reaction mixtures. In particularly preferred embodiments, the macromolecule can be a peptide, such as a single protein, a protein-protein complex, or a multi-subunit protein.

When the spacer or linker region contains exactly two cleavage sites that are differentially cleaved by two different mass spectrometric techniques, the cross-linker can be referred to as a dual cleavable cross-linking technology (DUCCT) cross-linker.

A. DUCCT Cross-Linkers

The cross-linkers have the general formula:

Formula I.

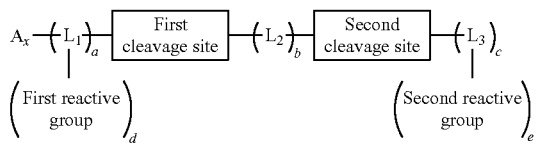

In some forms of Formula I, a, b, and c are independently integers between 0 and 20, inclusive, with the proviso that a and b are each at least 1; preferably, a, b, and c are 1.

In some forms of Formula I, d and e are independently integers between 1 and 20, inclusive; preferably d and e are 1.

The remaining components of the cross-linkers are described in more detail below.

1. Cleavage Sites

In some forms of Formula I, the spacer or linker region contains a first cleavage site and a second cleavage site. The first cleavage site and second cleavage site are independently bonds, or chemical groups containing bonds that are differentially cleaved by two different mass spectrometric techniques. Preferably, the bonds in the cleavage site are low energy bonds that can be cleaved in the gas-phase in a mass spectrometer. Examples of such bonds include amide bonds preferably, between proline and aspartate), nitrogen-nitrogen hydrazone bond, a C—Cα bond in peptides, mono-oxidized thioether bonds, urea-based, and nitrogen-carbon bonds vicinal to an amide bond. Examples of these bonds are shown below:

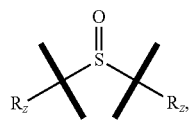

mono-oxidized thioether bond:
urea-based:

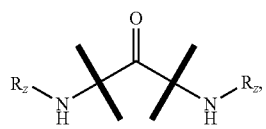

and
nitrogen-carbon bonds vicinal to an amide bond:

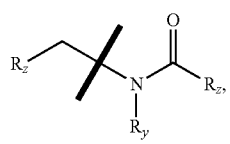

wherein each Rz can be a substituted alkyl, or unsubstituted alkyl, substituted aryl, or unsubstituted aryl, and Ry can be hydrogen, substituted alkyl, unsubstituted alkyl, substituted aryl, or unsubstituted aryl, and the bold lines indicate the cleavable low energy bonds.

wherein each Rz can be a substituted alkyl, or unsubstituted alkyl, substituted aryl, or unsubstituted aryl, and Ry can be hydrogen, substituted alkyl, unsubstituted alkyl, substituted aryl, or unsubstituted aryl, and the bold lines indicate the cleavable low energy bonds. In some forms, the chemical groups containing a bond that can be cleaved have the formula:

Pro-X                                                    Formula II wherein, Pro is proline, and X is preferably aspartate. As shown in Formula II, the bond that is being cleaved is the amide bond between $N_{Pro}$—$C_X$, wherein $N_{Pro}$ and $C_X$ indicate that the nitrogen and carbon atoms in the amide bond are from the proline and X residues, respectively. Preferably, the first cleavage site contains a chemical group defined by Formula II (Pro-X), as described above. Preferably, the second cleavage site is a nitrogen-nitrogen hydrazone bond. Most preferably, the first cleavage site and second cleavage site contain a chemical group defined by Formula II (Pro-X), as described above, and a nitrogen-nitrogen hydrazone bond, respectively.

Two different mass spectrometric fragmentation techniques that can be used to differentially cleave the first cleavage site and second cleavage site include, but are not limited to: collision induced dissociation (CID), electron transfer dissociation (ETD), electron capture and dissociation (ECD) Preferably, the two selected fragmentation techniques are CID and ETD. Preferably, the first cleavage site contains a bond that is cleaved by CID, and the second cleavage site contains a bond that is cleaved by ETD.

2. Sub-Linkers

In some forms of Formula I, the linker or spacer region contains sub-linkers denoted as $L_1$, $L_2$, and $L_3$. In some forms, each occurrence of $L_1$, $L_2$, and $L_3$ is independently an amino acid, —C(O)-unsubstituted heteroaryl-, —C(O)-substituted heteroaryl-, -unsubstituted aryl-(CO)—, -substituted aryl-(CO)—, —C(O)NH—, —C(O)NR'—, —NR'C(O)—, —C(O)O—, —OC(O)—, —C(O)OCH$_2$—, —SO$_2$NR'—, —CH$_2$R'—, —O—, —NR'H—, —NR'—, —OCONH—, —NHCOO—, —NHCONH—, —NR'CONH—, —NHCONR'—, —NR'CONR'—, —CHOH—, —CR'OH—, unsubstituted alkyl (such as unsubstituted $C_1$-$C_{20}$ alkyl, unsubstituted $C_1$-$C_{10}$ alkyl, unsubstituted $C_1$-$C_5$ alkyl), substituted alkyl (such as substituted $C_1$-$C_{20}$ alkyl, substituted $C_1$-$C_{10}$ alkyl, substituted $C_1$-$C_5$ alkyl), unsubstituted alkylene (such as unsubstituted $C_1$-$C_{20}$ alkylene, unsubstituted $C_1$-$C_{10}$ alkylene, unsubstituted $C_1$-$C_5$ alkylene), substituted alkylene (such as substituted $C_1$-$C_{20}$ alkylene, substituted $C_1$-$C_{10}$ alkylene, substituted $C_1$-$C_5$ alkylene), substituted alkenyl (such as substituted $C_1$-$C_{20}$ alkenyl, substituted $C_1$-$C_{10}$ alkenyl, substituted $C_1$-$C_5$ alkenyl), unsubstituted alkenyl (such as unsubstituted $C_1$-$C_{20}$ alkenyl, unsubstituted $C_1$-$C_{10}$ alkenyl, unsubstituted $C_1$-$C_5$ alkenyl), substituted alkylamino (such as substituted $C_1$-$C_{20}$ alkylamino, substituted $C_1$-$C_{10}$ alkylamino, substituted $C_1$-$C_5$ alkylamino), unsubstituted alkylamino (such as unsubstituted $C_1$-$C_{20}$ alkylamino, unsubstituted $C_1$-$C_{10}$ alkylamino, unsubstituted $C_1$-$C_5$ alkylamino), substituted carbonyl (such as substituted $C_1$-$C_{20}$ carbonyl, substituted $C_1$-$C_{10}$ carbonyl, substituted $C_1$-$C_5$ carbonyl), or unsubstituted carbonyl (such as unsubstituted $C_1$-$C_{20}$ carbonyl, unsubstituted $C_1$-$C_{10}$ carbonyl, unsubstituted $C_1$-$C_5$ carbonyl); an affinity group; or a combination thereof; and R' is hydrogen, halogen (F, Cl, Br, I), hydroxyl, unsubstituted alkyl (such as unsubstituted $C_1$-$C_{20}$ alkyl), substituted alkyl (such as substituted $C_1$-$C_{20}$ alkyl), substituted alkylene (such as substituted $C_1$-$C_{20}$ alkylene), unsubstituted alkylene (such as unsubstituted $C_1$-$C_{20}$ alkylene), substituted alkenyl (such as substituted $C_1$-$C_{20}$ alkenyl), unsubstituted alkenyl (such as unsubstituted $C_1$-$C_{20}$ alkenyl), substituted alkylamino (such as substituted $C_1$-$C_{20}$ alkylamino), unsubstituted alkylamino (such as unsubstituted $C_1$-$C_{20}$ alkylamino), substituted carbonyl (such as substituted $C_1$-$C_{20}$ carbonyl), or unsubstituted carbonyl (such as unsubstituted $C_1$-$C_{20}$ carbonyl), an aryl group, or a heterocyclic group. Preferably, $L_1$ contains aspartate, or lysine-glycine-aspartate; preferably, $L_2$ is —C(O)-unsubstituted heteroaryl-, wherein the unsubstituted heteroaryl is pyridine; and $L_3$ is preferably -unsubstituted aryl-(CO)—, wherein the unsubstituted aryl is phenyl.

3. Terminal Groups

In some forms of Formula I, the linker or spacer region contains a terminal group denoted A. In some forms, $A_x$ can be absent, one or more amino acids, —C(O)—$(CH_2)_n$—O-substituted aryl-substituted alkyl-, —C(O)—$(CH_2)_n$—O-unsubstituted aryl-substituted alkyl-, —C(O)—$(CH_2)_n$—O-substituted heteroaryl-substituted alkyl-, —C(O)—$(CH_2)_n$—O-unsubstituted heteroaryl-substituted alkyl-, —C(O)—$(CH_2)_n$—, —C(O)NH—, —C(O)NR'—, —NR'C(O)—, —C(O)O—, —OC(O)—, —C(O)OCH$_2$—, —SO$_2$NR'—, —CH$_2$R'—, —O—, —NR'H—, —NR'—, —OCONH—, —NHCOO—, —OCONR'—, —NR'COO—, —NHCONH—, —NR'CONH—, —NHCONR'—, —NR'CONR'—, —CHOH—, —CR'OH—, unsubstituted alkyl (such as unsubstituted $C_1$-$C_{20}$ alkyl, unsubstituted $C_1$-$C_{10}$ alkyl, unsubstituted $C_1$-$C_5$ alkyl), substituted alkyl (such as substituted $C_1$-$C_{20}$ alkyl, substituted $C_1$-$C_{10}$ alkyl, substituted $C_1$-$C_5$ alkyl), unsubstituted alkylene (such as unsubstituted $C_1$-$C_{20}$ alkylene, unsubstituted $C_1$-$C_{10}$ alkylene, unsubstituted $C_1$-$C_5$ alkylene), substituted alkylene (such as substituted $C_1$-$C_{20}$ alkylene, substituted $C_1$-$C_{10}$ alkylene, substituted $C_1$-$C_5$ alkylene), substituted alkenyl (such as substituted $C_1$-$C_{20}$ alkenyl, substituted $C_1$-$C_{10}$ alkenyl, substituted $C_1$-$C_5$ alkenyl), unsubstituted alkenyl (such as unsubstituted $C_1$-$C_{20}$ alkenyl, unsubstituted $C_1$-$C_{10}$ alkenyl, unsubstituted $C_1$-$C_5$ alkenyl), substituted alkylamino (such as substituted $C_1$-$C_{20}$ alkylamino, substituted $C_1$-$C_{10}$ alkylamino, substituted $C_1$-$C_5$ alkylamino), unsubstituted alkylamino (such as unsubstituted $C_1$-$C_{20}$ alkylamino, unsubstituted $C_1$-$C_{10}$ alkylamino, unsubstituted $C_1$-$C_5$ alkylamino), substituted carbonyl (such as substituted $C_1$-$C_{20}$ carbonyl, substituted $C_1$-$C_{10}$ carbonyl, substituted $C_1$-$C_5$ carbonyl), or unsubstituted carbonyl (such as unsubstituted $C_1$-$C_{20}$ carbonyl, unsubstituted $C_1$-$C_{10}$ carbonyl, unsubstituted $C_1$-$C_5$ carbonyl), an affinity group, or a combination thereof, wherein n is an integer between 1 and 10, inclusive; R' is hydrogen, halogen (F, Cl, Br, I), hydroxyl, unsubstituted alkyl (such as unsubstituted $C_1$-$C_{20}$ alkyl), substituted alkyl (such as substituted $C_1$-$C_{20}$ alkyl), substituted alkylene (such as substituted $C_1$-$C_{20}$ alkylene), unsubstituted alkylene (such as unsubstituted $C_1$-$C_{20}$ alkylene), substituted alkenyl (such as substituted $C_1$-$C_{20}$ alkenyl), unsubstituted alkenyl (such as unsubstituted $C_1$-$C_{20}$ alkenyl), substituted alkylamino (such as substituted $C_1$-$C_{20}$ alkylamino), unsubstituted alkylamino (such as unsubstituted $C_1$-$C_{20}$ alkylamino), substituted carbonyl (such as substituted $C_1$-$C_{20}$ carbonyl), or unsubstituted carbonyl (such as unsubstituted $C_1$-$C_{20}$ carbonyl). Preferably, $A_x$ is one or more amino acids, —C(O)—$(CH_2)_n$—O-substituted aryl-substituted alkyl-, —C(O)—$(CH_2)_n$—O-unsubstituted aryl-substituted alkyl-, —C(O)—$(CH_2)_n$-0-substituted heteroaryl-substituted alkyl-, —C(O)—$(CH_2)_n$—O-unsubstituted heteroaryl-substituted alkyl-, —C(O)—$(CH_2)_n$—, an affinity group, or a combination thereof n is 3 or 4.

4. Reactive Groups

In some forms of Formula I, the cross-linker contains two or more reactive groups. In general, a reactive group in the cross-linker participates in a chemical reaction with another reactive group in another molecule, such as a macromolecule, resulting in the covalent attachment of the cross-linker to molecule, such as a macromolecule. Preferably, reactions by two or more reactive groups in the cross-linker with two or more different sites in another molecule results in a cross-linking of the molecule.

In some forms of Formula I, each occurrence of a first reactive group and a second reactive group is independently N-hydroxysuccinimide ester, sulfo-N-hydroxysuccinimide ester, maleimide, sulfydryl, hydroxyl, amine, azide, glycidyl, aldehyde, diazirine, diazoacetate ester, acrylate, nitrophenyl ester, nitrile, or a combination thereof. In some forms, the first reactive group and second reactive group are the same. In some forms, the first reactive group and second reactive group are different.

The reactive groups can be located on pendant groups and/or part of a main chain of the cross-linker. The distance of the reactive group is a major concern for MS-cleavable crosslinkers. Most of the cleavable crosslinker reactive distances are very large and have been a major concern, resulting in non-specific labeling. The disclosed crosslinkers preferably have a distance ~11.0-12 range A between the reactive groups. In some forms, the distance between at least two reactive groups is between 9 Å and 25 Å, inclusive, 9 Å and 18 Å, inclusive, 9 Å and 13 Å, inclusive, or between 11 Å and 12 Å, inclusive. The distance referred to is the through-space distance between the reactive groups, which is distinct from the through-bond distance that involves the distance formed by bonds connecting the two reactive groups. The through-space distance can be determined from one or more geometry optimized structures of molecular models of the cross-linkers. However, in native biological settings a cross-linker having a through-space distance between reactive groups of between 11 Å and 12 Å, inclusive. Sometimes cross-links at sites separated by longer distances, for example between 22 Å and 38 Å.

B. Tagged-DUCCT Crosslinkers

Dual mass spectrometry cleavable crosslinker compositions which include an enrichment reagent (i.e., affinity tagged) are provided. The enrichment reagent is preferably is one member of a pair of molecules with bind to each other with specificity as disclosed herein. These compositions allow enrichment of the cross-linked peptides from a large-scale experiment using the binding partner of the enrichment (used as a capture agent), used as a: "fishing hook" to capture the crosslinker-enrichment reagent complex. The "fishing hook" is used to isolate the affinity tagged crosslinker from a mixture of molecules. (See FIG. 1B). The capture reagent can be immobilized in a purification system, for example biotin-avidin affinity chromatography. The enrichment reagent is attached to the crosslinker, directly or indirectly, via a cleavable bond, preferably, a photo-cleavable bond, or a cis-diol bond. Both CID and ETD cleavage sites are incorporated into the crosslinker using the same chemistry for the dual mass spectrometry cleavable crosslinker disclosed above, i.e., the crosslinker that does not include an affinity group. The cleavable bond that is involved in attaching enrichment reagent to the crosslinker, is cleaved to release the cross-linked peptides from the capture agent (for example, avidin beads). In a preferred embodiment, the bond is photocleavable, or is mild oxidative cleavable bond (cis-diol). A more preferred embodiment is a photocleavable biotin-DUCCT (PC-biotin-DUCCT) crosslinker. The photo-cleavable crosslinker is released from the biotinylated peptide after UV-light exposure and will release the cross-linked peptides from an avidin bead, for example, used to capture the biotinylated DUCCT crosslinker.

Subsequent CID and ETD MS/MS will generate signature mass spectra for identification of cross-linked peptides. The CID and ETD-MS/MS will identify the cross-linked peptides according to the dual mass spectrometry cleavable crosslinker and biotinylated dual mass spectrometry cleavable crosslinker.

Figure 4:
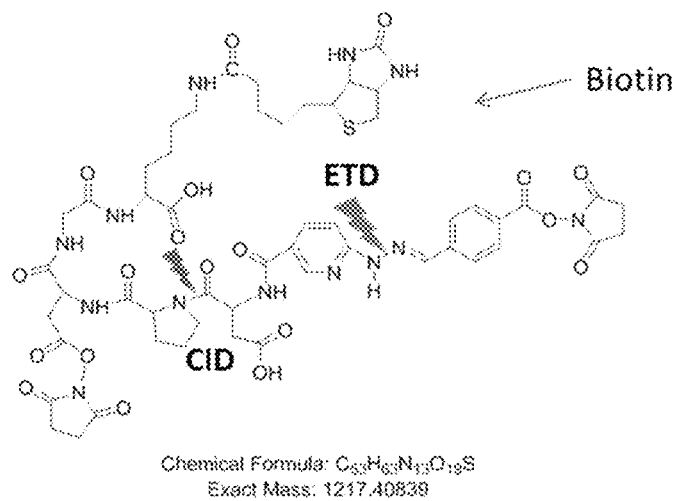
FIG. 4 shows the structure of the DUAL cleavable cross-linker with enrichment reagent biotin (DUCCT-biotin).
Figure 5:
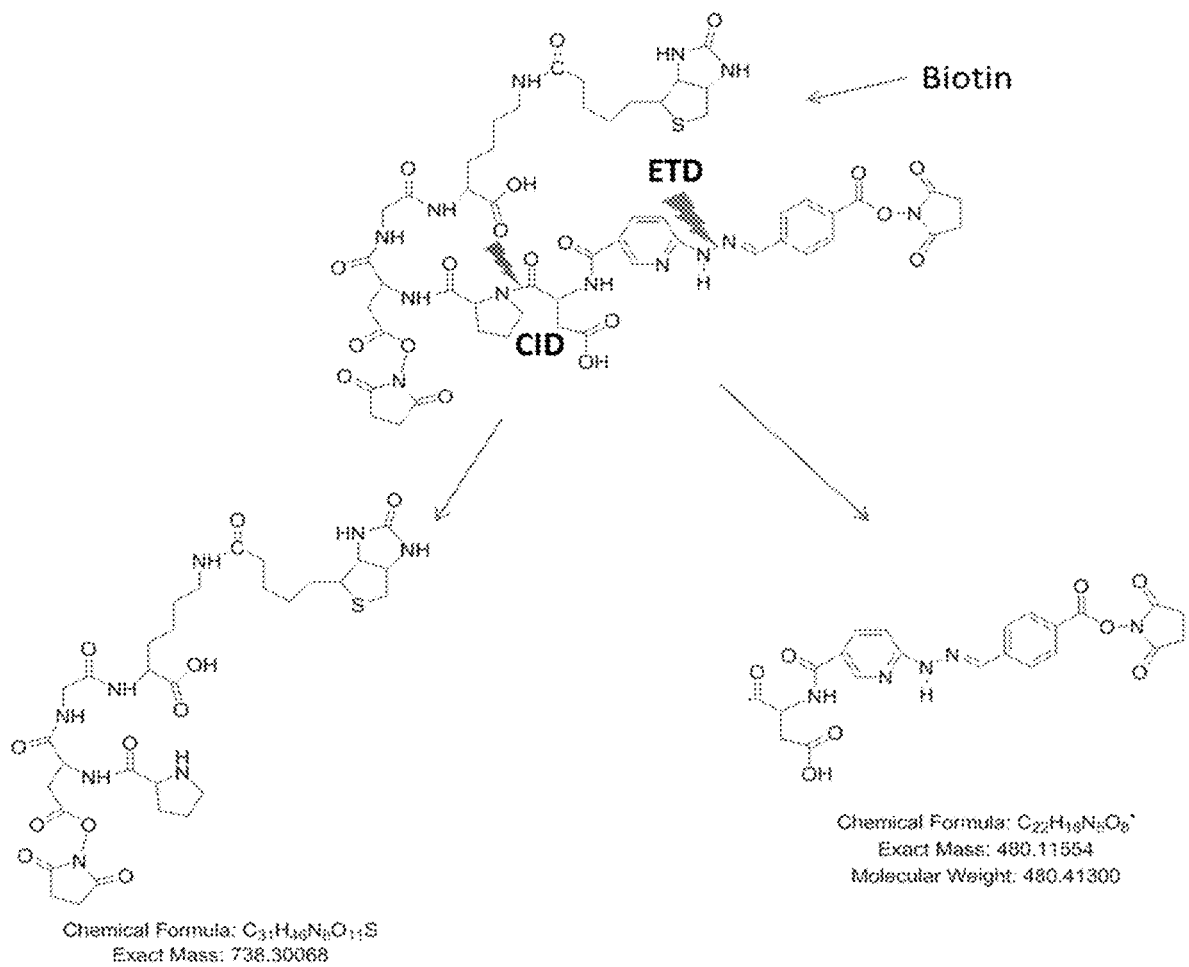
FIG. 5 shows the predicted fragment signatures from the CID-MS/MS cleavage.

FIG. 4 shows that CID and ETD cleavage sites incorporated into a biotin tagged DUCCT crosslinker (biotin-DUCCT crosslinker) using the same chemistry disclosed for DUCCT crosslinker. After CID MS/MS, it will produce efficient cleavage at DP bonds. Efficient cleavage at CID-MS/MS cleavage sites produces m/z 739.36, which corresponds to the breakage of DP bonds. Two reactive groups N-hydroxysuccinimide ester losses were also observed. The predicted fragment signatures after CID-MS/MS are shown in FIG. 5. ETD-MS/MS will not generate any fragmentation signature until the crosslinker is conjugated with peptides or proteins.

Figure 6:
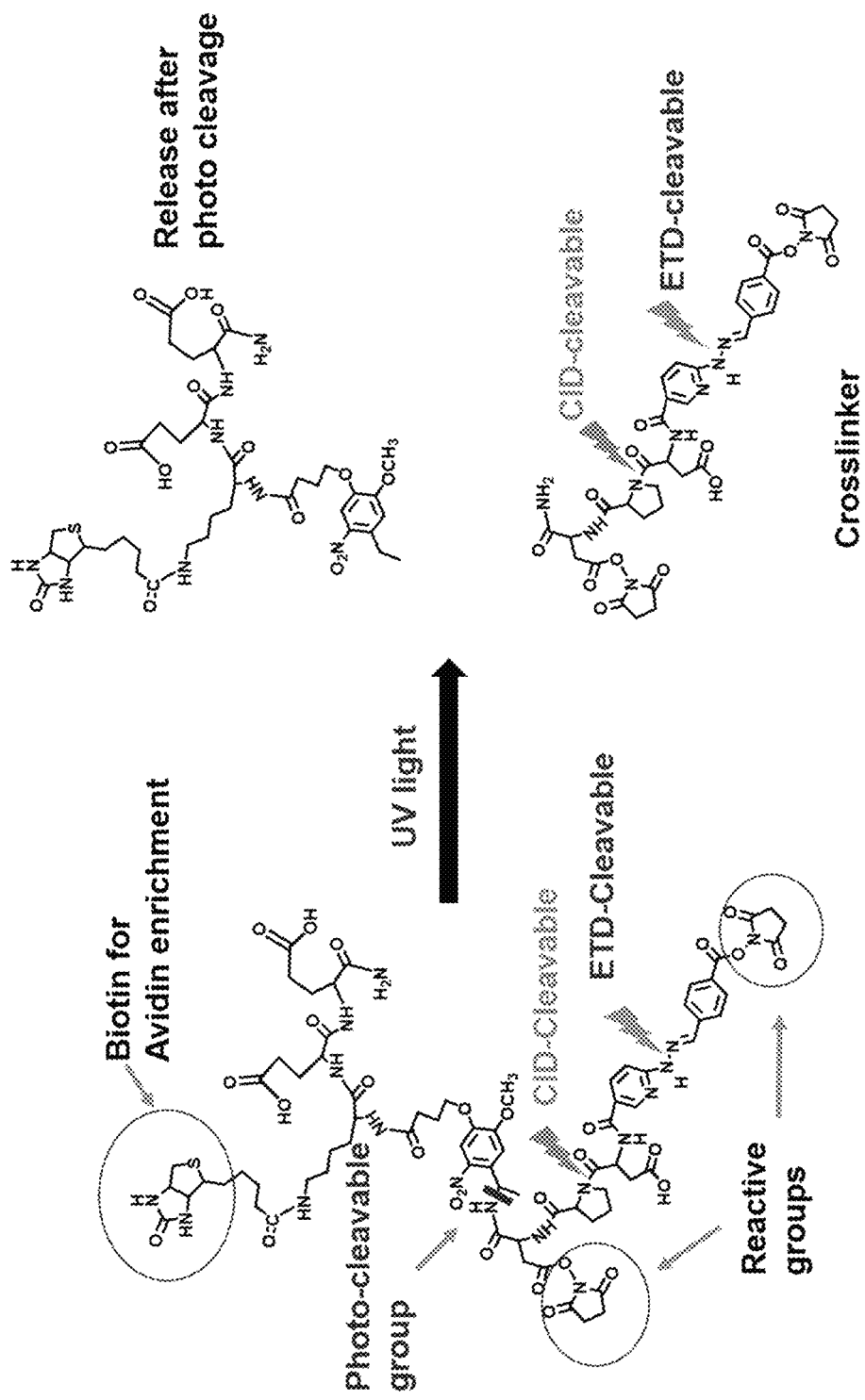
FIG. 6 illustrates the photo-cleavable biotinylated cross-linker.

FIG. 6 shows a biotinylated cross-linker containing biotin (PC-biotin-DUCCT crosslinker) that can be used as an affinity group to enrich a reaction mixture with cross-linked protein or peptides, using biotin-avidin affinity chromatography. The cross-linked peptides or protein can be eluted from the avidin bead and subsequent UV light exposure will release the biotinylated part of the compound and cross-linked portion will be attached to the peptides.

1. Enrichment Reagents

Compounds that can be used as enrichment reagents include one member of any two molecules known to bind to each other with high affinity, examples of which are disclosed further herein for example, affinity tags. Affinity tags are known in the art (reviewed in Kimble, et al., Curr Protoc Protein Sci. 2013; 73: Unit-9.9).

The affinity group includes for example, known protein purification tags, antibodies or antigen-binding fragment thereof, an RNA or protein shaped to specifically interact with the target (e.g., an RNA- or peptide-aptamer), a small molecule or element with specific binding affinity (e.g., biotin which binds streptavidin, or iron which is bound by the transferrin receptor) or a ligand for a cell a cell-surface receptor or cell-surface antigen.

Examples of affinity groups include, but are not limited to, chemical moieties such as alkyne, azide, and glycidyl; and affinity molecules such as biotin, hemagglutinin, streptavidin, fusion proteins, and antibodies.

Useful affinity molecules also include, polypeptide purification tags, which are known in the art and include, but are not limited to His tags which typically include six or more, typically consecutive, histidine residues; FLAG tags, which typically include haemagglutinin (HA) for example, YPYDVP (SEQ ID NO:1), YPYDVPDYA (SEQ ID NO:2); E-tag (GAPVPYPDPLEPR (SEQ ID NO:3)), a peptide recognized by an antibody, and affinity purification of recombinant proteins, a peptide which binds to streptavidin, or a peptide recognized by an antibody. These peptide tags are bound by antibodies specific to them, which are commercially available. Other peptide tags include. AviTag, a peptide allowing biotinylation by the enzyme BirA and so the protein can be isolated by streptavidin (GLNDIFEAQK-IEWHE (SEQ ID NO:4)), Calmodulin tag, polyglutamate tag, a peptide binding efficiently to anion-exchange resin such as Mono-Q (EEEEEE (SEQ ID NO:5)), TC tag, a tetracysteine tag that is recognized by FlAsH and ReAsH biarsenical compounds (CCPGCC (SEQ ID NO:6)). HA tagged peptide in DUCCT can be enriched using HA antibody magnetic beads which will reduce the sample complexity significantly by enriching the DUCCT cross-linked peptides. Avi-tag affinity technology will be an ideal candidate for incorporation in the DUCCT with different reactive groups other than primary amines.

The crosslinkers can be linked to ligands which bind to specific aptamers. Aptamers are oligonucleotide or peptide sequences with the capacity to recognize virtually any class of target molecules with high affinity and specificity. Aptamers bind to targets such as small organics, peptides, proteins, cells, and tissues. Unlike antibodies, some aptamers exhibit stereoselectivity. An aptamer which binds the specific ligand can then be used as a fishing hook to enrich for crosslinkers bound to its ligand.

Figure 1B:
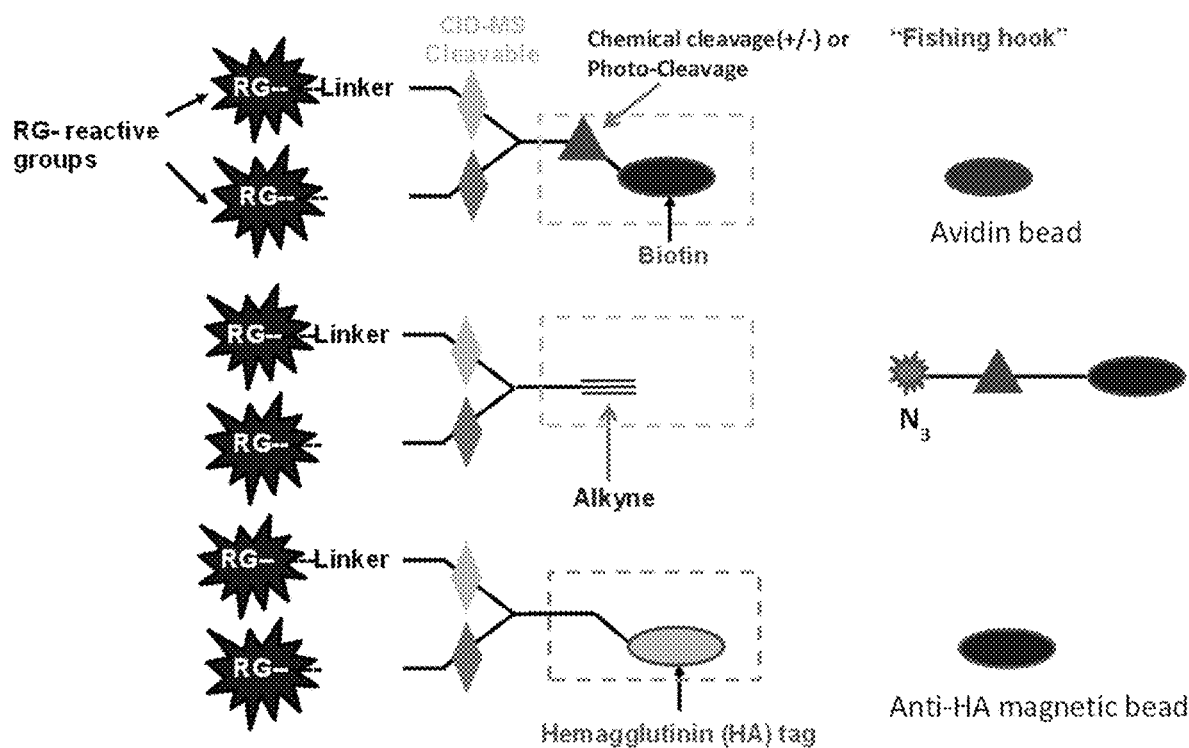
FIG. 1B illustrates the design of a dual cleavable crosslinker with an affinity tag.

Methods of using purification tags to facilitate macromolecule purification are known in the art and include, for example, a chromatography step wherein the tag reversibly binds to a chromatography resin or using magnetic beads which display the binding partner (capture agent) for the enrichment reagent (See FIG. 1B).

2. Design of Enrichment Reagents to DUCCT Crosslinkers

An affinity group can be attached directly or indirectly to a cross-linker at any of $A_x$, $L_1$, $L_2$, and $L_3$ described above, preferably via covalent attachment, i.e., $A_x$, $L_1$, $L_2$, and $L_3$ can include an affinity group. Preferably, the attachment of an affinity group to a cross-linker involves a covalent bond that is cleaved differentially from the bonds in the cleavage sites of the linker or spacer region of a cross-linker. The covalent bond can be cleaved photolytically (i.e., photo-cleavable), chemically, thermally, enzymatically, hydrolytically, or using mass spectrometric techniques such as CID, ETD, and ECD. It is to be understood that the covalent bond involved in attaching an affinity group to a cross-linker is selected such that it is not cleaved by the any of the methods used to fragment the cleavage sites in the linker or spacer region of the cross-linker. Preferably, the covalent bond is photocleavable.

Preferred embodiments of the cross-linker described above for Formula I, include crosslinkers as define in Formula I with the exception that a, b, c, d, and e are each 1, i.e., the cross-linker has the formula:

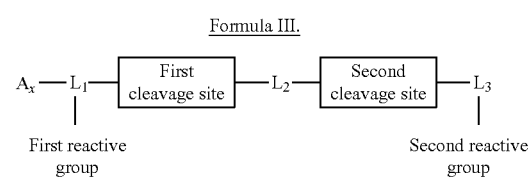

Formula III.

In some forms, the cross-linker is as described above for Formula III, with the exception that $L_1$ is aspartate.

In some forms, the cross-linker is as described above for Formula III, with the exception that the first cleavage site has the formula:

Pro-X          Formula II wherein, Pro is proline, and X is preferably aspartate. As shown in Formula II, the bond that is being cleaved is the amide bond between $N_{Pro}$—$C_X$, wherein $N_{Pro}$ and $C_X$ indicate that the nitrogen and carbon atoms in the amide bond are from the proline and X residues, respectively.

In some forms, the cross-linker is as described above for Formula III, with the exception that $L_2$ is —C(O)-unsubstituted heteroaryl-, or —C(O)-substituted heteroaryl.

In some forms, the cross-linker is as described above for Formula III, with the exception that the second cleavage site is a nitrogen-nitrogen hydrazone bond.

In some forms, the cross-linker is as described above for Formula III, with the exception that $L_3$ is -unsubstituted aryl-C(O)—, or -substituted aryl-C(O)—.

In some forms, the cross-linker is as described above for Formula III, with the exception that the first reactive group and second reactive group are N-hydroxysuccimide ester.

In some forms, the cross-linker is as described above for Formula III, with the exception that $A_x$ is glycine.

In some forms, the cross-linker is as described above for Formula III, with the exception that $A_x$ is selected from one or more amino acids, —C(O)—$(CH_2)_n$—O-substituted aryl-substituted alkyl-, —C(O)—$(CH_2)_n$—O-unsubstituted aryl-substituted alkyl-, —C(O)—$(CH_2)_n$—O-substituted heteroaryl-substituted alkyl-, —C(O)—$(CH_2)_n$—O-unsubstituted heteroaryl-substituted alkyl-, —C(O)—$(CH_2)_n$—, an affinity group, or a combination thereof. In some forms, n is 3, 4, or a combination thereof. In some forms, the one or more amino acids are glycine and lysine.

In some forms, the cross-linker is as described above for Formula III, with the exception that $A_x$ is selected from one or more amino acids, —C(O)—$(CH_2)_n$—, and an affinity group. In some forms, n is 4. In some forms the one or more amino acids are glycine and lysine. In some forms the affinity group is biotin.

In some forms, the cross-linker has the formula:

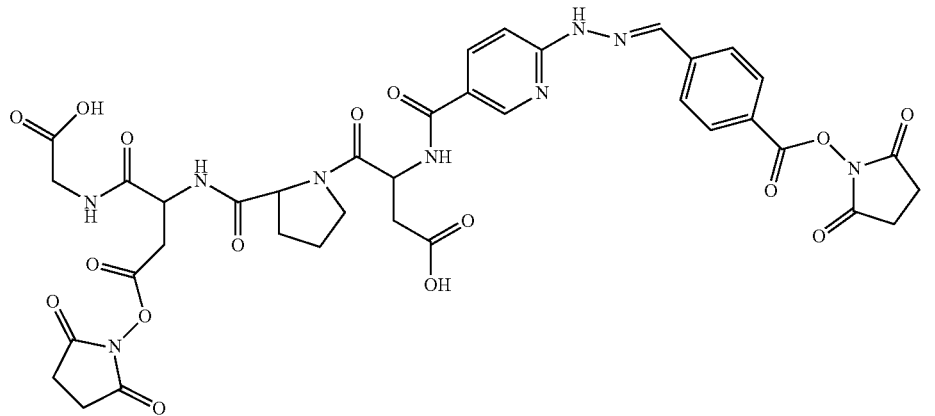

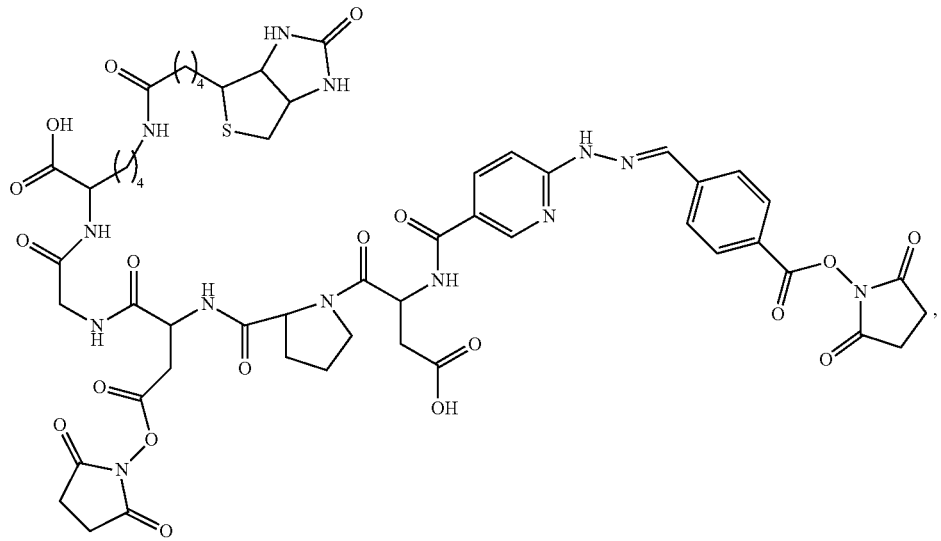

,

-continued

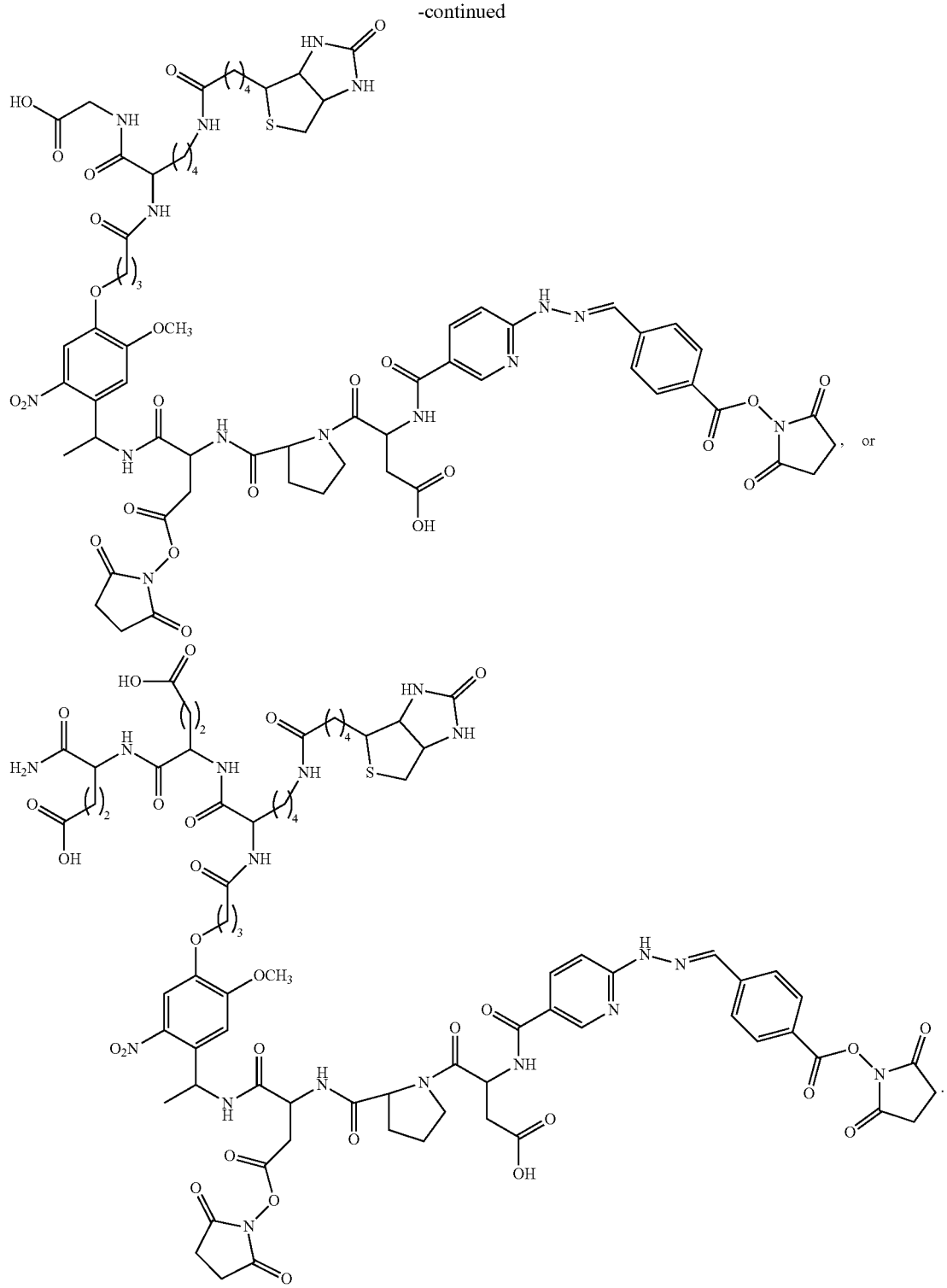

, or

Every compound within the above definition is intended to be and should be considered to be specifically disclosed herein. Further, every subgroup that can be identified within the above definition is intended to be and should be considered to be specifically disclosed herein. As a result, it is specifically contemplated that any compound or subgroup of compounds can be either specifically included for or excluded from use or included in or excluded from a list of compounds. For example, any one or more of the compounds described herein, with a structure depicted herein, or referred to in the Tables or the Examples herein can be specifically included, excluded, or combined in any combination, in a set or subgroup of such compounds. Such specific sets, subgroups, inclusions, and exclusions can be applied to any aspect of the compositions and methods described here. For example, a set of compounds that specifically excludes one or more particular compounds can be used or applied in the context of compounds per se (for example, a list or set of compounds), compositions including the compound (including, for example, pharmaceutical compositions), any one or more of the disclosed methods, or combinations of these. Different sets and subgroups of compounds with such specific inclusions and exclusions can be used or applied in the context of compounds per se, compositions including one or more of the compounds, or any of the disclosed methods. All of these different sets and subgroups of compounds—and the different sets of compounds, compositions, and methods using or applying the compounds—are specifically and individual contemplated and should be considered as specifically and individually described. As an example, any of the natural amino acids or unnatural amino acids, as defined above, can be specifically included or excluded, as a group or individually, from any position in the compounds per se (for example, a list or set of compounds).

III. Methods of Making and Using

Although cross-linkers containing two cleavage sites have been described, the cleavage sites in these cross-linkers contain the same cleavable bonds, and are cleaved by the same mass spectrometric technique (Tang, et al., *Mol. Biosyst.* 2010, 6(6), 939-947). However, the DUCCT cross-linkers disclosed herein (containing two cleavage sites that are cleaved differentially by two different mass spectrometric techniques) can be distinguished from these prior cross-linkers, and to the best of our knowledge, have not been previously described. This can be attributed, in part, to the complexity involved in the synthesis and/or to a lack of recognition, in the field, of the advantages of utilizing cross-linkers containing two or more cleavage sites that are differentially cleaved by at least two different mass spectrometric techniques. Synthesizing dual cleavable cross-linker with differential mass spectrometric techniques is a huge challenge due to the difficulty in conjugating these bonds and subsequent incorporation of reactive groups. Although the gas-phage cleavage properties of these bonds were known, never before have the bonds been utilized to develop a cross-linker. This challenge has been solved by providing a synthetic route with innovative protection and de-protection of acidic amino acid residues in the DUCCT cross-linker.

In some forms, the cross-linkers can be synthesized via methods such as solid or solution phase peptide synthesis, preferably solid phase peptide synthesis (SPPS). The amino acids to be used in the synthesis generally contain protecting groups, such as Fmoc, that are deprotected prior to reacting with a subsequent amino acid, upon completion of the synthesis of the cross-linkers, or both. In the course of the synthesis, a reactive group such as NHS can be introduced into the linker, preferably for conjugation of lysine residues in peptides. Further, two or more gas phase cleavable bonds are added in the design. The first cleavable bond can be a Pro-Asp bond (DP), which is cleaved by low energy CID. The second cleavable bond can be nitrogen-nitrogen hydrazone bond, which is cleaved by ETD. Both of the cleavable bonds are sandwiched in between two NHS ester reactive groups (FIG. 3). Preferably, the distance of the reactive group this DUCCT cross-linker is between 9 Å and 25 Å, most preferably, between about 11.0 Å and 12 Å, inclusive (FIG. 3).

The examples provide details on how to synthesize cross-linkers containing cleavage sites, such as DUCCT cross-linkers, which are differentially cleaved by different mass spectrometric techniques.

In a non-limiting example of a SPPS, an amine protected amino acid, such as Fmoc-Gly can be coupled to a resin. Alternatively, a resin can be obtained that already includes a protected amino acid, such as the Fmoc-Gly-Wang resin (Anaspec, Inc.). Next, the Fmoc protecting group is cleaved followed by the addition of another protected amino acid, such as Fmoc-Asp(O-2-PhiPr), a super-sensitive form of Fmoc-Asp. This can be followed by coupling with proline and then the typical form of Asp using Fmoc Asp-OtBu. It is noted that the coupling of proline with the typical form of Asp, forms a DP amide bond that can be cleaved by a mass spectrometric technique such as CID. The free amine of this Asp residue can be coupled to a reagent such as Hydralink 6-Fmoc-HNA (Fmoc-6-hydrazinonicotinic acid). After Fmoc is released from the Hydralink 6-Fmoc-HNA, the free amine in the hydrazine group can be reacted with a bivalent molecule that contains an aldehyde and a carboxylic acid group, for example. An exemplary bivalent molecule can be 4-formylbenzoic acid. Reaction between the free amine and aldehyde gives rise to a hydrazone link. It is noted that the hydrazone link contains a nitrogen-nitrogen bond that forms another bond that can be differentially cleaved by a mass spectrometric technique such as ETD. The unreacted carboxylic acid group in the bivalent molecule forms a first carboxylic acid group in the cross-linker. Next, the protecting group of the super-sensitive Asp can be removed to form a second carboxylic acid group. These two carboxylic acids can be activated using a cross-linking agent such as dicyclohexyl carbodiimde (DCC). A reactive group, such as N-hydroxy succinimide (NHS) can be added to react with the activated carboxylic acids to form NHS esters. The final compound can be cleaved from the resin to form a free cross-linker, and the cross-linker isolated.

In a non-limiting example, an affinity group, such as biotin, can be added to the cross-linker by inserting lysine (biotin) between the glycine and the supersensitive aspartate residue using Fmoc lys(biotin) (Novabiochem).

The general synthesis scheme described herein can be used to conjugate differential tandem mass spectrometry-based cleavable bonds and subsequent incorporation of reactive groups, such as NHS esters, by solid-phase synthesis using a peptide synthesizer.

The cross-linkers described herein, can be used in the characterization of the structures of single macromolecules, macromolecule complexes, and multi-subunit macromolecules in analytical methods such as mass spectrometry. Macromolecule complexes are used herein to refer to interactions/associations between a macromolecule and a second molecule which result in the macromolecule being bound to the second molecule. The second molecule in some embodiments is a macromolecule, and in other embodiments, the second molecule is not a macromolecule. The interactions can be covalent association or a non-covalent association. Examples of interactions that result in a macromolecule being bound to a second molecule to form a complex include covalent bonds, dipole interactions, electrostatic forces, hydrogen bonds, hydrophobic interactions, ionic bonds, and/or van der Waals forces.

Examples of single macromolecules include peptide, proteins, glycoproteins, and nucleic acids. Examples of macromolecule complexes include protein-protein complexes; and protein-non-protein complexes, such as protein-carbohydrate complexes, and protein-nucleic acid complexes.

Examples of multi-subunit macromolecules include multimeric proteins. Biological samples, such as different kind of cells can be characterized to determine structures of proteins, or protein complexes utilizing the cross-linkers described herein. Examples of macromolecule or a complex containing a macromolecule (macromolecule complex), can be a receptor/ligand complex; biotin avidin complex; peptide/S ribonuclease complex; digoxigenin/anti-digoxigenin antibody complex; complimentary oligonucleotide pair complex and antibody/ligand complex.

The cross-linkers can be used to map protein-protein interactions of a protein complex. This mapping includes contacting a cross-linker described herein with a protein complex under conditions in which two or more reactive groups in the cross-linker react with a reactive group in the protein complex to form a cross-linked protein complex; optionally digesting the protein complex with an enzyme such as trypsin to form peptides and/or peptide fragments; and using mass spectrometry ($MS^z$) to identify the protein and/or peptide fragments, wherein Z can be an integer between 1 and 4, inclusive, such as 1, 2, 3, or 4.

The location of the cross-linkers with defined distances between reactive groups, introduces distance constraints on the location of the cross-linked sites within the macromolecules, which provide insights about the three-dimensional structures of the macromolecules. These distance constraints can also be included in structure refinement programs to produce three-dimensional structural models of macromolecules of interest. In some forms, the insights provide information about the structure of a protein-protein complex, such as protein complexes in cell signaling cascades in diseased or normal cells to find target biomarkers and potential therapeutics for several inflammatory disease including cancers.

Figure 2A:
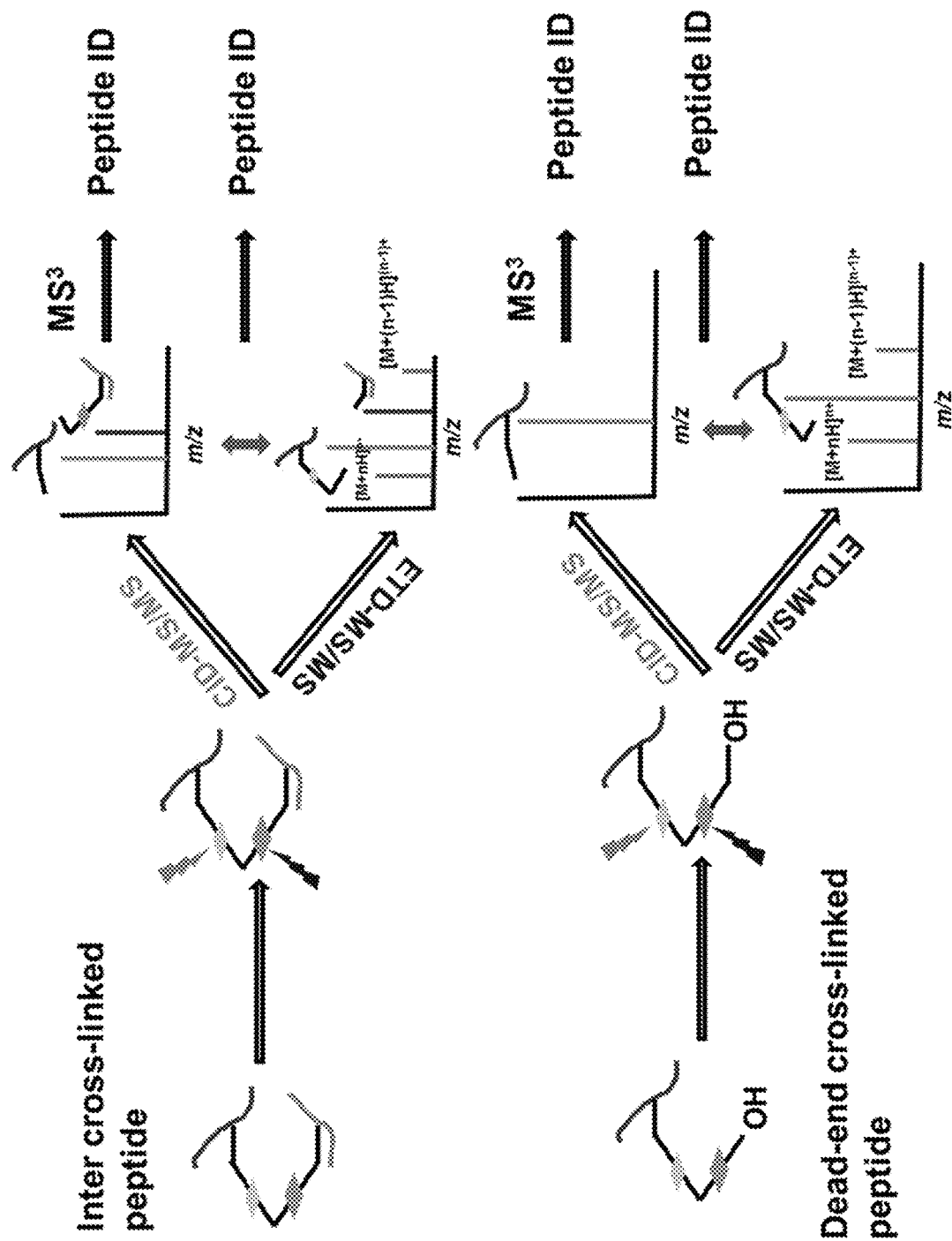
Figure 2B:
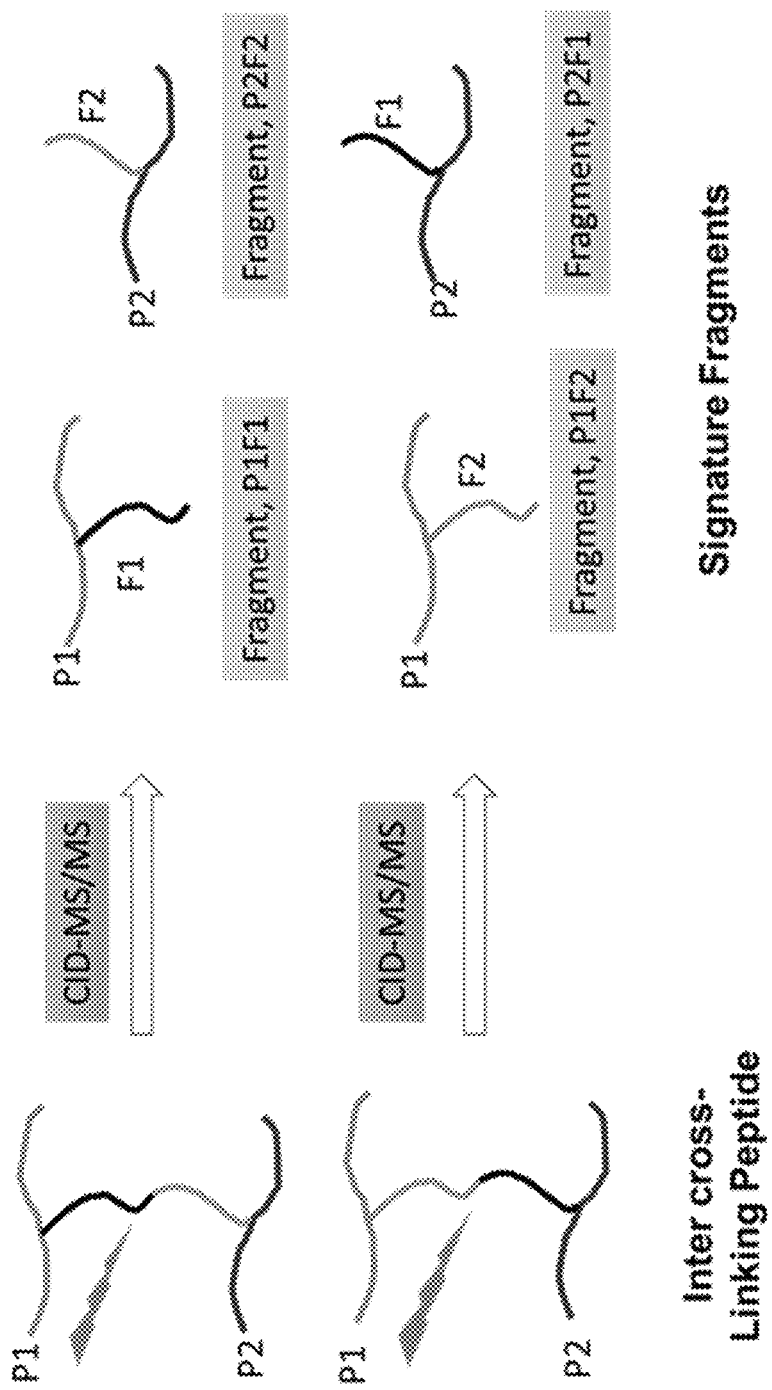

The disclosed compositions and methods provide a number of advantages over known chemical crosslinkers and methods employing them. For example, the disclosed DUCCT crosslinker with two differential cleavable bonds facilitate the structural analysis of macromolecules with a greater degree of certainty, compared to other known cross-linkers. Schematics of the designs of exemplary crosslinkers are shown in FIGS. 1A and 1B. The cross-linker contains two gas-phase cleavable bonds which can be selectively cleaved using CID or ETD. After CID MS/MS, an inter-crosslinked peptide will produce two peptide peaks attached with cross-linker pieces, whereas ETD MS/MS will produce two peaks of the same cross-linked peptide with different cross-linker portions (FIGS. 2A-2C). In addition, ETD will produce charge reduced peaks of precursor masses. This will also help to identify the charge states of precursor m/z, even if a low resolution mass spectrometer is being used. These two signature spectra will unambiguously identify cross-linked peptides. Furthermore, dead end a peptide will generate one peptide with residual crosslinker mass due to the hydrolysis of one reactive group in the crosslinker (FIG. 2A, bottom). Their CID and ETD mass spectra will generate two complementary fragmentation signatures of one cross-linked peptide (FIGS. 2B and 2C).

In FIG. 2B, CID cleaves in a specific site (D-P bond) of a crosslinker and produces two peptide ions (P1 and P2) with fragmented crosslinker residue (F1 and F2) (signature fragments). In FIG. 2C, ETD cleaves in different site (N—N bond) other than CID and produces two peptide ions (P1 and P2) with added different crosslinker residues (F1 and F2) (signature fragments) and neutralized precursor ions. A further mass spectrometric step ($MS^3$) can be used for CID only identification. Both CID and ETD will identify peptide sequence without further MS/MS.

The DUCCT crosslinkers disclosed herein including the embodiments tagged with an enrichment reagent can be contacted with a biological sample as exemplified in the Examples.

Prior to contacting the biological sample with the DUCCT cross-linkers with the cross-linkers can be dissolved in a suitable solvent in which the components of the cross-linker (reactive groups, cleavage sites, terminal groups, affinity groups, etc.) are stable. A suitable solvent can be dimethyl sulfoxide (DMSO). The cross-linkers are then contacted in a small volume with the biological sample in a suitable buffer, such as phosphate buffered saline (PBS) under conditions in which two or more reactive groups in the cross-linker react with a reactive group in a macromolecule present in the biological sample (e.g. peptide, protein, protein-protein complex, etc.) to form a cross-linked macromolecule (e.g. cross-linked peptide, protein, protein complex, etc.). The biological sample containing the cross-linked macromolecules can be purified, as needed, and the cross-linked macromolecules isolated for structural analyses. The structural analyses can be performed using an analytical method such as liquid chromatography-tandem mass spectrometry (LC-MS/MS).

EXAMPLES

Experimental Details

Materials.

Neurotensin (pyr-LYENKPRRPYIL (SEQ ID NO:13)) was purchased from Anaspec, Inc (San Jose, Calif.). Two proteins, bovine serum albumin (BSA) and ubiquitin were obtained from Sigma-Aldrich (St. Luis, Mo.) and other chemicals like Tris-HCl, dimethyl sulfoxide (DMSO), ammonium bicarbonate and formic acid were also purchased from Sigma-Aldrich (St. Luis, Mo.). LC-MS grade methanol and acetonitrile were obtained from VWR (Radnor, Pa.). A reducing agent dithiothreitol (Biorad, CA), an alkylating agent iodo-acetamide (Sigma-Aldrich, MO) and a protease enzyme trypsin (Promega, Madison, Wis.) were utilized to digest the proteins properly. For synthesis of crosslinker, the raw materials like Fmoc amino acids were supplied by EMD Millipore (Billerica, Mass.), the formylbenzoic acid by Sigma-Aldrich (St. Luis, Mo.) and Fmoc hydralink 6-Fmoc-HNA reagent from Advanced Automated Peptide Protein Technology (Louisville, Ky.), DCC reagent from Life Technologies (Pittsburgh, Pa.). 18 MiliQ water was used for all the studies and was obtained from a water filtering system purchased from Aries Filterworks, West Berlin, N.J.

Cross-linking of Neurotensin (Peptide) The developed cross-linking agent (DUCCT) was prepared in dimethyl sulfoxide (DMSO). The neurotensin was treated with DUCCT in 1:10 molar ratio along with PBS buffer (pH 7.2). The reaction was permitted to continue for 30 mins at ambient temperature, and then the reaction was quenched with 50 mM Tris-HCl buffer (PH 8.0). The samples were desalted by zip tip (Thermo Scientific, Waltham, Mass.) and properly dried by speed vacuum, and finally reconstituted in 0.1% formic acid. Crosslinked peptide samples were analyzed by a LTQ (Linear Ion Trap Quadrupole) Velos Pro mass spectrometer.

Cross-Linking of Ubiquitin and BSA.

The reaction of protein (ubiquitin/BSA) with crosslinking agent (DUCCT) was carried out into 1:50 molar ratio along with PBS buffer (pH 7.2). The reaction was performed for 30 mins and quenched by 50 mM Tris-HCl buffer. A concentrator (3 KDa MWCO cut off, Thermo scientific, USA) was used to take out the excess amount of crosslinking agent. The protein concentration was determined using the BCA protein assay. Next, the crosslinked proteins were digested in both in-gel and in-solution methods using trypsin followed by reduction and alkylation.

In-Solution Digestion.

The crosslinked protein was reduced by 10 mM dithiothreitol (Biorad, CA), alkylated by 55 mM iodoacetamide (Sigma-Aldrich, MO), and then digested by trypsin (Promega, Madison, Wis.). The protein-trypsin ratio was set 50:1 and the sample was incubated for overnight at 37° c. The tryptic digestion was quenched by using 0.1% FA. The sample was dried by using speed vacuum, desalted using zip tip, re-suspended in 0.1% FA and finally transfer to LC vial for analyzing the sample by mass spectrometry.

In-Gel Digestion.

The crosslinked protein was prepared with laemmli buffer (Bio-rad, OH), and heated for 5 mins at 95° C. for denaturing the proteins. Next, the protein sample was loaded on 10% SDS-PAGE gel. By utilizing the electrophoresis technique, separation of proteins were observed according to the molecular weight. The bands that found from gel were digested followed by excision, dehydration, reduction and alkylation. After tryptic digestion, the peptides were eluted by 50% acetonitrile, dried properly by speed vacuum and reconstitute in 0.1% of FA.

Instrumental Analysis.

For sample analysis, an LTQ Velos Pro mass spectrometry coupled with a UHPLC (ultimate 3000, Dionix, USA) was utilized. Cross-linked peptides were separated by reverse phase chromatography using a nano-viper analytical C18 column (Acclaim™ Pep Map™ 100 C18 LC Columns, Thermo scientific). Separation was executed with a binary gradient system where the organic and aqueous mobile phase contain 95% acetonitrile and 98% water respectively. The nano-column flow rate and injection volume were set 300 nl/min and 5 µl (partial injection mode).

For ionization, the ESI (Electrospray ionization) source was applied where spray voltage and heated capillary temperature were fixed 2.0 v and 275° c. respectively. Full scans spectra (AGC 3×104) were obtained from 350 to 2000 m/z and data dependent MS/MS spectra (AGC 1×104) was found from five most intense precursor ions. Dynamic exclusion time was fixed 30 ms for separating consecutive ions. Data acquisition was set for 90 mins and X-Caliber software was utilized for data processing.

In CID fragmentation mode, activation energy was set 45% along with isolation width 1.5 Da, activation Q 0.25, and activation time 10 ms For ETD operation mode, emission current, reagent ion electron energy and reagent ion source CI pressure, and source temperature of the reagent ion source were set to 50 UA, −70 v, 20 psi and 110° C. respectively. The ETD reaction time was fixed 80 ms with isolation width 2 Da. Direct infusion was also conducted in LTQ Valos Pro to analyze the cross-linked peptides.

Figure 16:
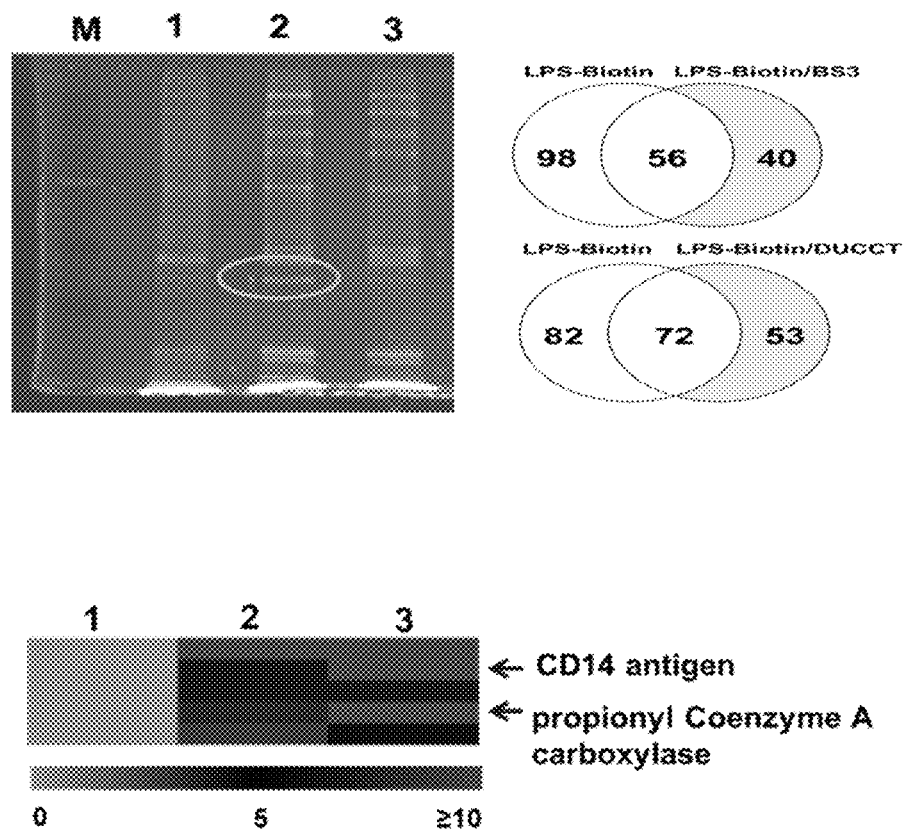
FIG. 16 shows a SDS-PAGE of biotin-avidin pulldown experiments (top-left), and Venn diagram (top-right) of number of protein identified. Heatmap (bottom panel) of few selected proteins identified exclusively in crosslinked samples after pulldown studies with avidin. M-Marker, 1-LPS biotin, 2. LPS-biotin/DUCCT. 3-LPS-biotin/BS3, Scale demotes to spectral counts.

LPS-Biotin Pulldown Studies:

LPS was purchased from Invivogen, CA and raw blue 264.7 was a gift from Dr. Michael B. Fessler lab at NIEHS, NIH. The cells were grown with DMEM (500 mL) media using 5 mL penstrap and 10% FBS and grown in 37° C. in a forma incubator (thermos scientific). After 80% confluency, cells were scrapped and collected in a 15 mL centrifuge tube with DMEM media. 25 µg of LPS-Biotin was added in the media (10 mL) and cells were incubated at 37 C for 15 min with mild stirring. After 30 min, two quick 500 µL PBS washes were done to remove the LPS. 10 mL of PBS buffer was added in the samples and in the solution 1 mg of BS3 was directly added. DUCCT crosslinker was added using the same amount (1 mg dissolve in 2 µL of DMSO). The solution was incubated for 30 min with mild sitting at room temp. After 30 minutes, 50 mM of 10 µL Tris-HCL was used to stop the reactions. Next, cells were washed with several times with PBS buffer. The cells were lysed with RIPA buffer (1 h) and centrifuged to collect the proteins. After that proteins were incubated with 50 µL dynabeads streptavidin (thermos scientific). After several wash with the PBS in a magnet stand, the proteins were eluted from the bead using 2× lamellae buffer. SDS-page gel were run and stained with sypro ruby (thermos scientific, pierce) (FIG. 16). The gel lane were cut, digested (24 sections for each lane) and analyzed by LC-MS/MS in Agilent XCT ETD mass spectrometer with CID and ETD-MS/MS fragmentations. Heat map was generated (FIG. 16). All MS/MS samples were analyzed using Spectrum Mill (Agilent, Santa Clara, Calif., USA; version Unknown). Spectrum Mill was set up to search the NCBInr.rodent database (selected for All, unknown version, 14227560 entries) using the digestion enzyme trypsin. Spectrum Mill was searched with a fragment ion mass tolerance of 0.70 Da and a parent ion tolerance of 2.5 Da. Scaffold (version Scaffold 4.3.2, Proteome Software Inc., Portland, Oreg.) was used to validate MS/MS based peptide and protein identifications. Peptide identifications were accepted if they could be established at greater than 80.0% probability by the Peptide Prophet algorithm (Keller, A et al Anal. Chem. 2002; 74(20):5383-92). Protein identifications were accepted if they could be established at greater than 95.0% probability and contained at least 1 identified peptide. Protein probabilities were assigned by the Protein Prophet algorithm (Nesvizhskii, Al et al Anal. Chem. 2003; 75(17):4646-58).

Example 1—Synthesis of the DUCCT Crosslinker

The cross linker was synthesized using Fmoc peptide synthesis reagents. The reactive group was used are N-hydroxy succinimide (NHS) for conjugation of lysines. Two gas phase cleavable bonds were added in the design. The first cleavable bond is a pro-asp bond (DP), which is found to be cleaved by low energy CID. The second cleavable bond, nitrogen-nitrogen hydrazone bond, which was reported for ETD cleavage. The CID and ETC cleavable bonds were sandwiched in between two NHS ester reactive groups which finally constituted a lysine reactive crosslinker (FIG. 3).

The cross linker was synthesized using Fmoc peptide synthesis reagents with an Applied Biosystems 431 Peptide Synthesizer at the 0.25 mmole scale. Fmoc Gly was first coupled to the resin followed by the supersensitive form of Fmoc Asp, Fmoc-Asp(O-2-PhiPr) or Fmoc glycine Wang resin (Anaspec. Inc) was followed by the Fmoc supersensitive Asp. This was then followed by coupling proline and then the typical form of Asp using Fmoc Asp-OtBu. The free amine of this Asp was coupled to Hydralink 6-Fmoc-HNA reagent. After Fmoc was released, 4-formylbenzoic acid was added which formed the hydrazone link and a terminal carboxylic acid. The protection group of the supersensitive asp was removed by 2% TFA in dichloromethane to create the second carboxylic acid. These two carboxylic acids were activated by DCC to which the NHS esters were then formed by adding 2 mmole N-hydroxysuccinimide (Aldrich) with the DCC. The final compound was cleaved from the resin by 95% TFA with 5% water for 1 hr. The product was precipitated with diethyl ether, centrifuged, the pellet dissolved in 0.1% TFA water and quickly lyophilized. The biotin form of the cross linker was synthesized as the first form by inserting lysine(biotin) between the glycine and the supersensitive aspartate residue using Fmoc lys(biotin) (Novabiochem).

The distance of the reactive group is a major concern for MS-cleavable crosslinkers. Most of the cleavable cross linker reactive distances are very large and has been a major concern due to the consequent non-specific labeling. However, for this DUCCT cross-linker design was selected such that the distance between the reactive groups was kept approximately in the 11.0-12 Å range (FIG. 3).

Figure 7:
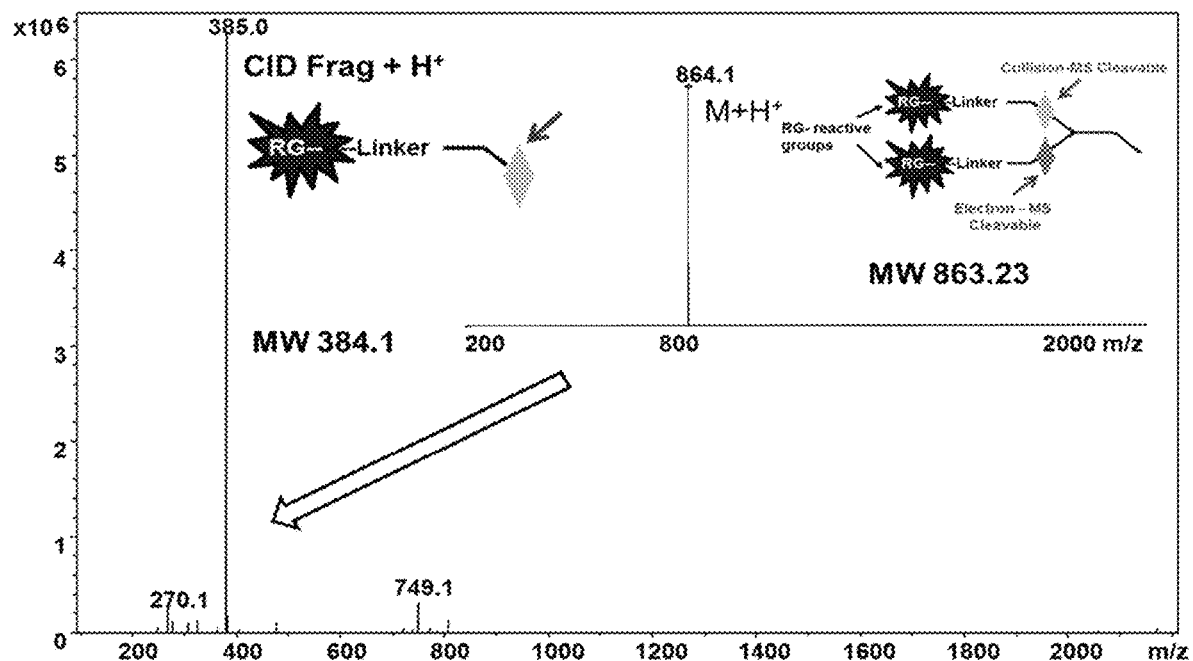
FIG. 7 shows efficient fragmentation is achieved in Asp-Pro peptide bond by CID.

The molecular weight of the crosslinker was first determined by MS. The molecular mass of crosslinker was 863.2358 Da. After fragmentation in CID the DUCCT crosslinker showed efficient cleavage at Asp-Pro (DP) peptide bonds (FIG. 7). It is also to note that the crosslinker will not be cleaved by ETD without conjugation with peptides since ETD is a charge dependent fragmentation. Primary amine side chain of lysine will react with the NHS ester reactive groups in the cross-linker forming an amide bond releasing the NHS esters from the crosslinker.

Figure 8A:
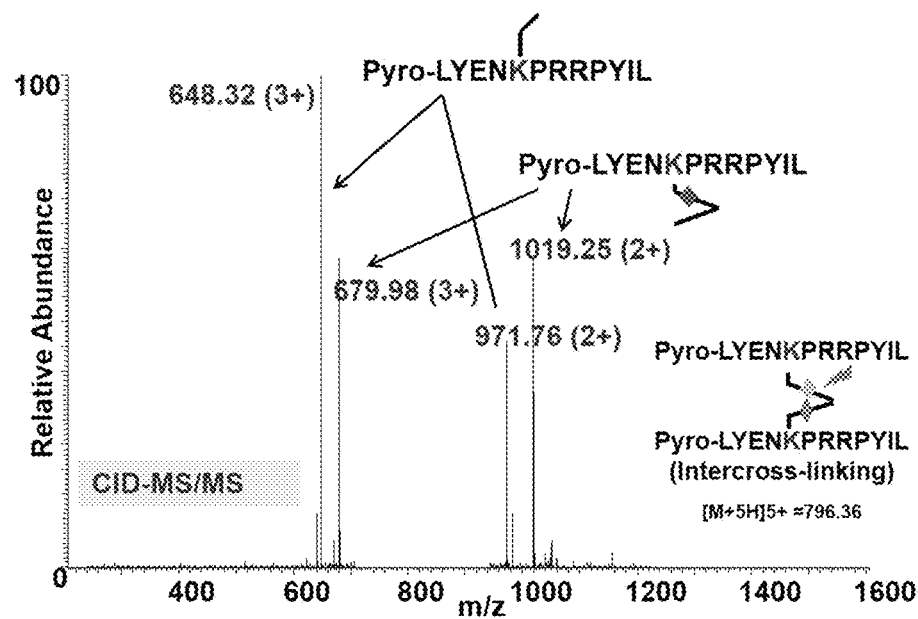
FIGS. 8A and 8B show CID (FIG. 8A) and ETD (FIG. 8B) mass spectra of cross-linked neurotensin peptide (SEQ ID NO: 7) dimer, with related cleavage products (SEQ ID NO. 14)

A model peptide, neurotensin, was treated with the cross-linker shown in FIG. 3. Neurotensin has one lysine residue and its N-terminal is blocked with pyro-glue modification. The crosslinker labeled efficiently and produced inter and dead-end residues. Two inter-crosslinked peptides were identified at m/z's 995.2577 (M+4H+) and 796.4076 (M+5H+) respectively. CID-MS/MS clearly showed cleavage at DP bond and ETD-MS/MS showed cleavage at the N—N bonds. In CID, two peptide ions with added cross-linker residues should be observed, and in ETD for inter cross-linking the same two peptide ions with different cross-linker residue masses should be observed. For neurotensin, two fragment peaks at m/z 971.76 and 1019.25 respectively were observed, which corresponds to the peptide mass and corresponding CID cleavage part of the crosslinker (FIG. 8A).

Figure 9:
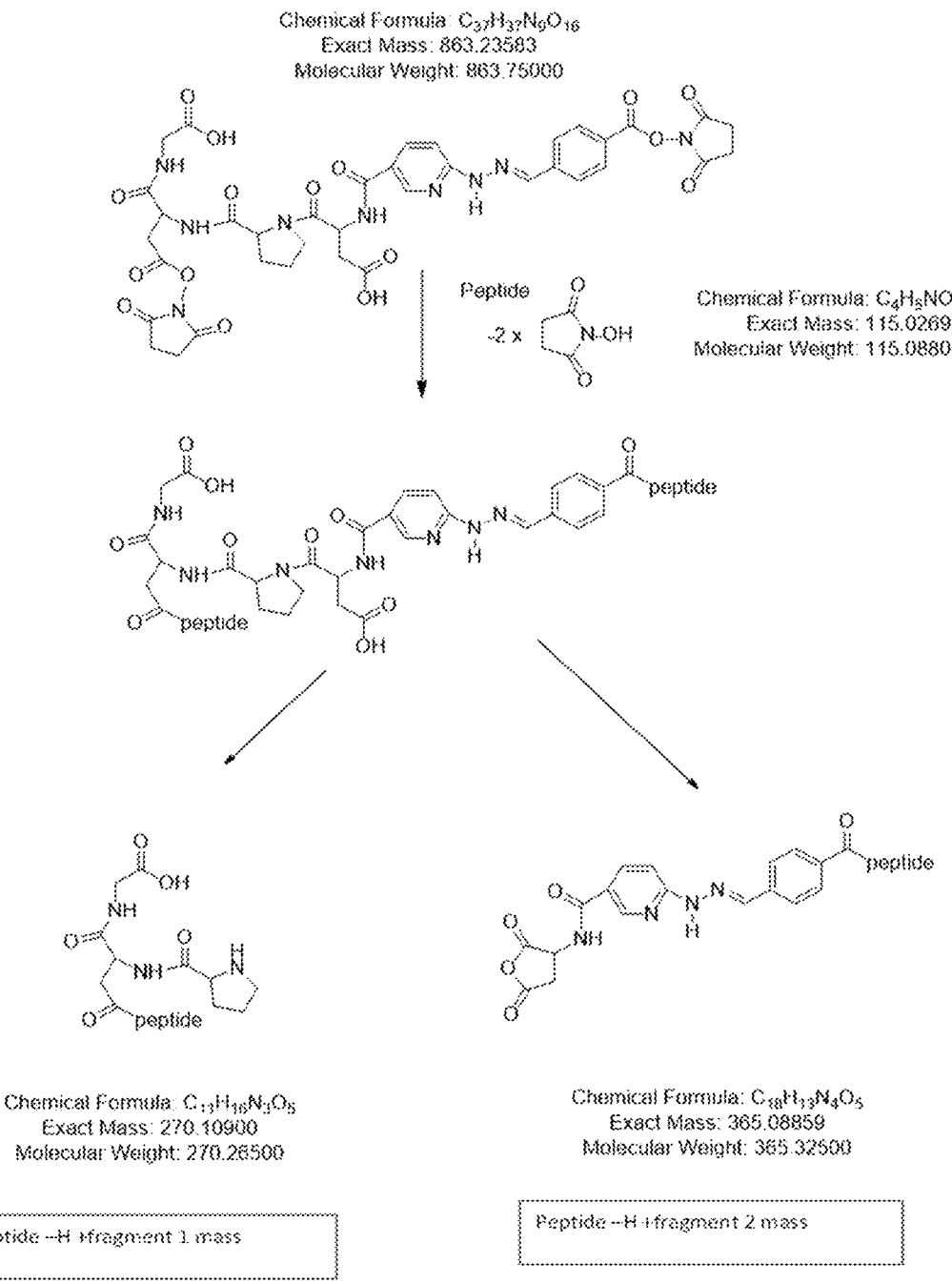
FIG. 9 shows the structure of DUCCT with CID cleaved signature fragments.

In addition, 3+ charge states of these peptides (m/z at 679.98 and 648.32) were also observed. Complete calculations are shown in Table 1 and FIG. 9. FIG. 9 shows the structure of dual mass spectrometry cleavable crosslinker with CID cleaved signature fragments. The crosslinker has two reacting groups (NHS ester). Loss of NHS groups occurred during cross-linking reactions with peptides. CID cleaved the Asp-Pro peptide bond of DUCCT and generated two fragments.

Figure 8B:
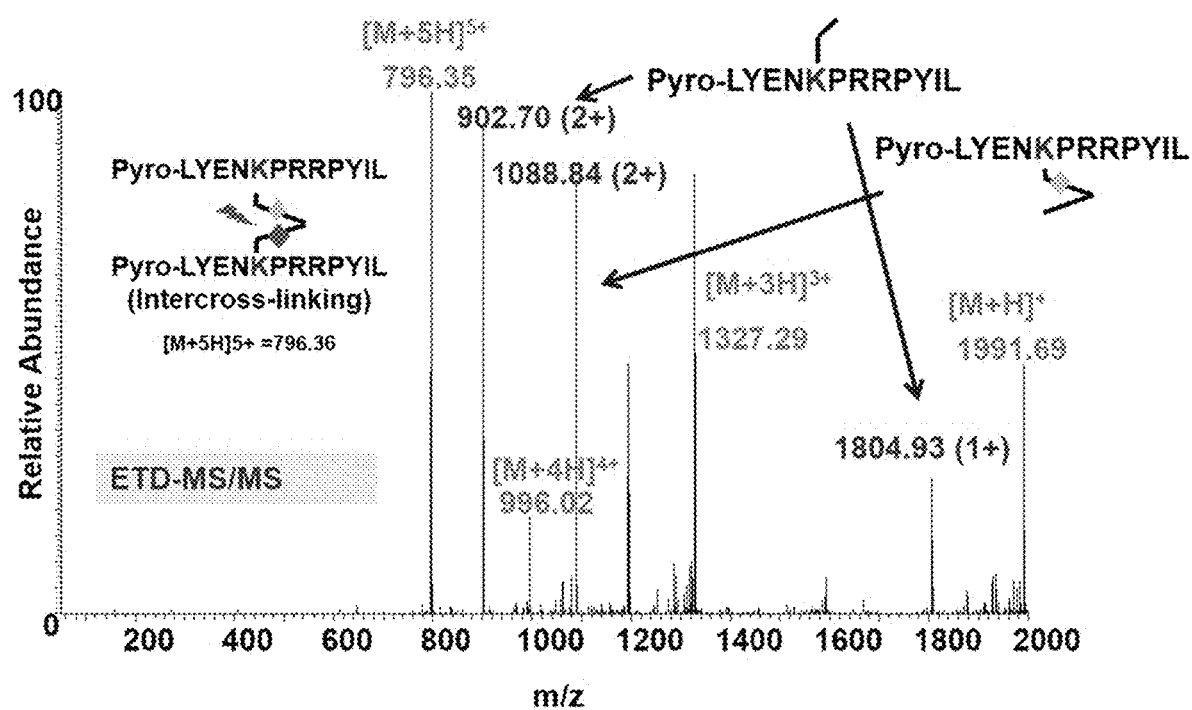

ETD clearly matched calculated masses with crosslinker residues. Charge reduced precursor ions were also observed with ETD, which clearly provided the proof of the charge states of the cross-linked peptides even though a high resolution mass spectrometer was not used for this study (FIG. 8B). These data clearly showed CID and ETD signatures of two same peptides after cross-linking experiments. These two signatures mass spectra of the same cross-linked peptides can identify cross-linked peptides confidently. Similar experiments were performed using bradykinin, also resulting in the identification of cross-linked peptides with a high degree of certainty.

TABLE 1

List of calculated masses and m/z value used to identify cross-linked reaction products. All the experimental m/z's are average due to the utilization of a LTQ Velos Pro MS.

|  | Exact Mass (2 decimal) | m/z |
| --- | --- | --- |
| Crosslinker (DUCCT) | 863.24 | 864.24 (1+) |
| CID Fragments | 384.13 | 385.13 (1+) |
|  | 479.11 | 480.11 (1+) |
| NHS (reactive group) | 114.02 |  |
| Neurotensin + DUCCT (Inter crosslink) | (1671.92 × 2)(2 peptides) + 863.24(Cross-linker) − (114.02 × 2) (2 leaving group) − 2 (2 Hydrogen) = 3977.04 | 1326.68 (3+) 995.26 (4+) 796.41 (5+) |
| Neurotensin + DUCCT (Dead-end) | 1671.92 (peptide) + 863.24(Cross-linker) − (114.02 × 2)(2 leaving group) + 17 (—OH) − 1 (1Hydrogen) = 2323.12 | 2324.12 (1+) 1162.56 (2+) 775.37 (3+) |
| Neurotensin + Fragment residue mass 1 (CID) | 1671.92 (peptide) + 270.11 (Fragment1) − 1(1Hydrogen) = 1940.03 | 1941.03 (1+) 971.02 (2+) 647.68 (3+) |
| Neurotensin + Fragment residue mass 2 (CID) | 1671.92 (peptide) + 365.09 (Fragment 2) − 1(1Hydrogen) = 2036.01 | 2037.02 (1+) 1019.01 (2+) 679.67 (3+) |
| Neurotensin + Fragment residue mass 1 (ETD) | 1671.92 (peptide) + 504.16 (Fragment 1) − 1(1Hydrogen) = 2075.08 | 2176.08 (1+) 1088.54 (2+) 726.03 (3+) |
| Neurotensin + Fragment residue mass 2 (ETD) | 1671.92 (peptide) + 132.04 (Fragment 2) − 1(1Hydrogen) = 1802.96 | 1803.96 (1+) 902.48 (2+) 601.99 (3+) |

Figure 10:
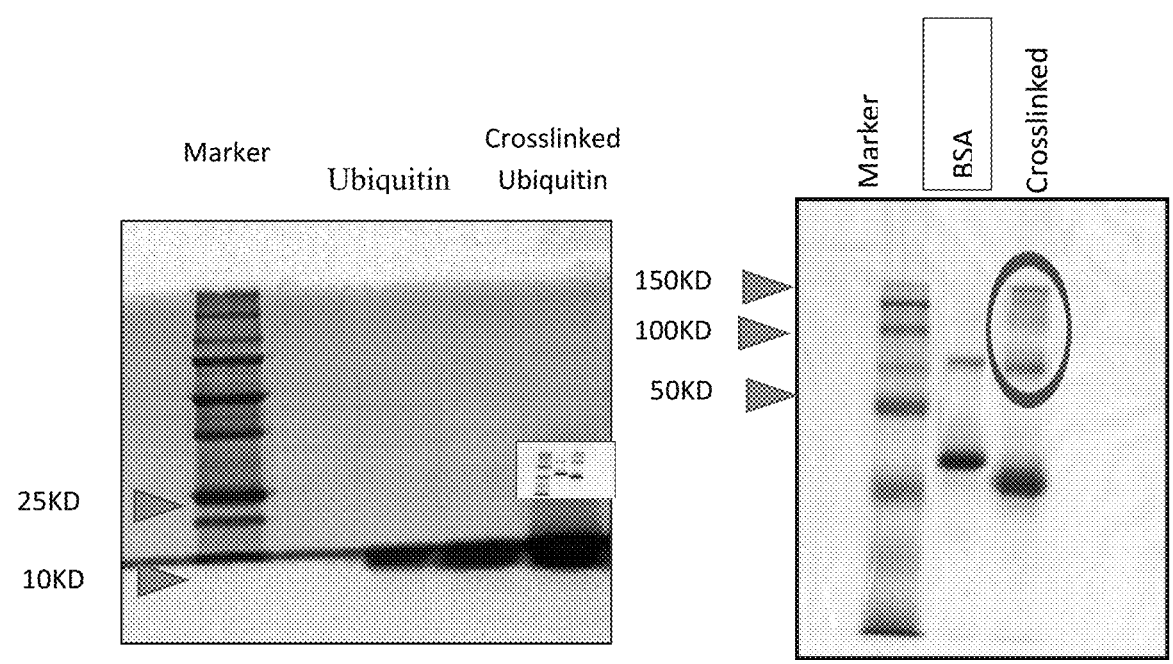
FIG. 10 show a SDS PAGE gel image of crosslinked ubiquitin (left) and BSA (right).
Figure 11:
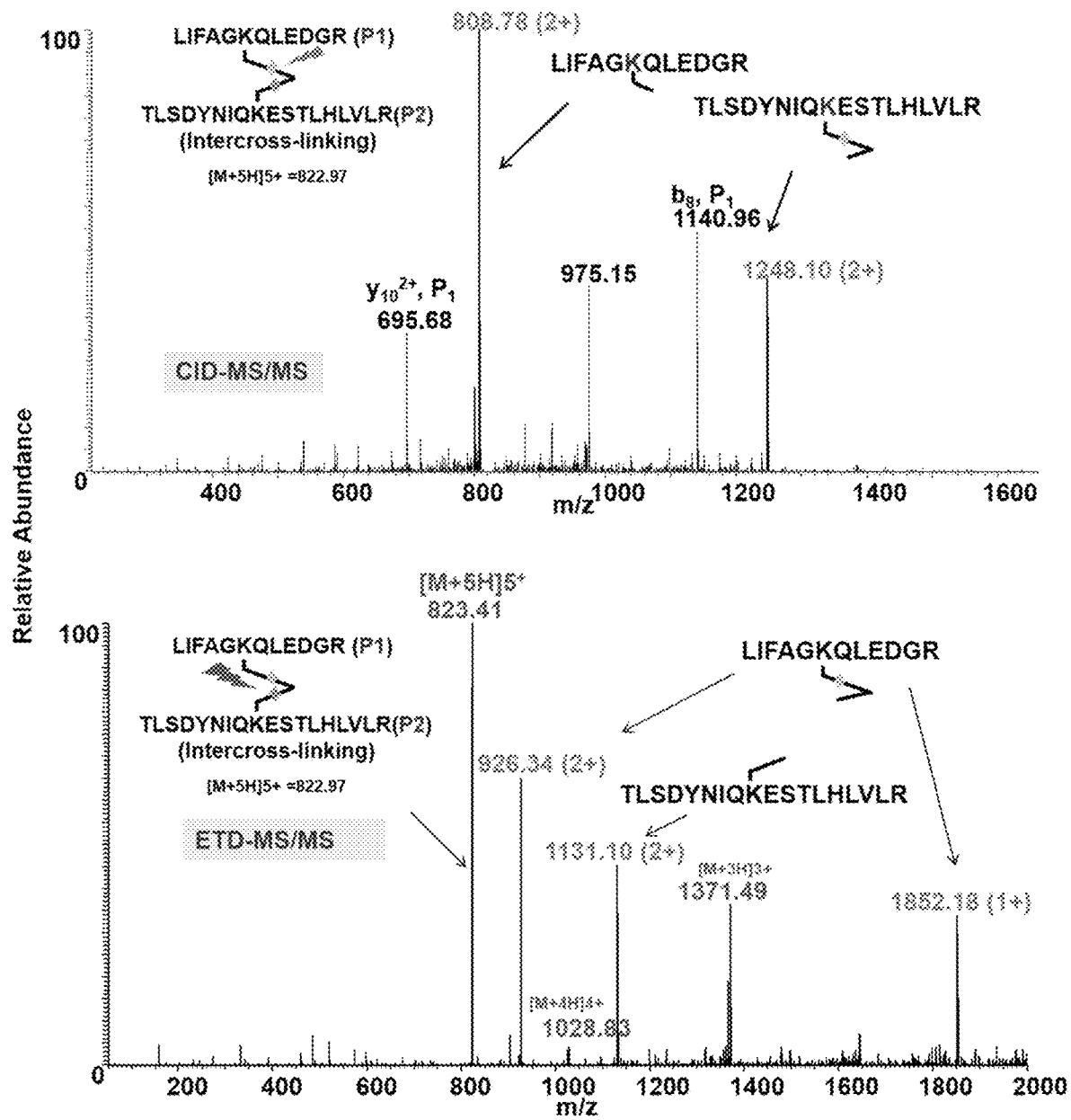
FIG. 11 shows an example of CID (upper panel) and ETD (lower panel) mass spectra of an inter crosslinked peptide derived from ubiquitin (SEQ ID NO: 8), and the related cleavage products (SEQ ID NO: 9 and SEQ ID NO: 10).
Figure 12:
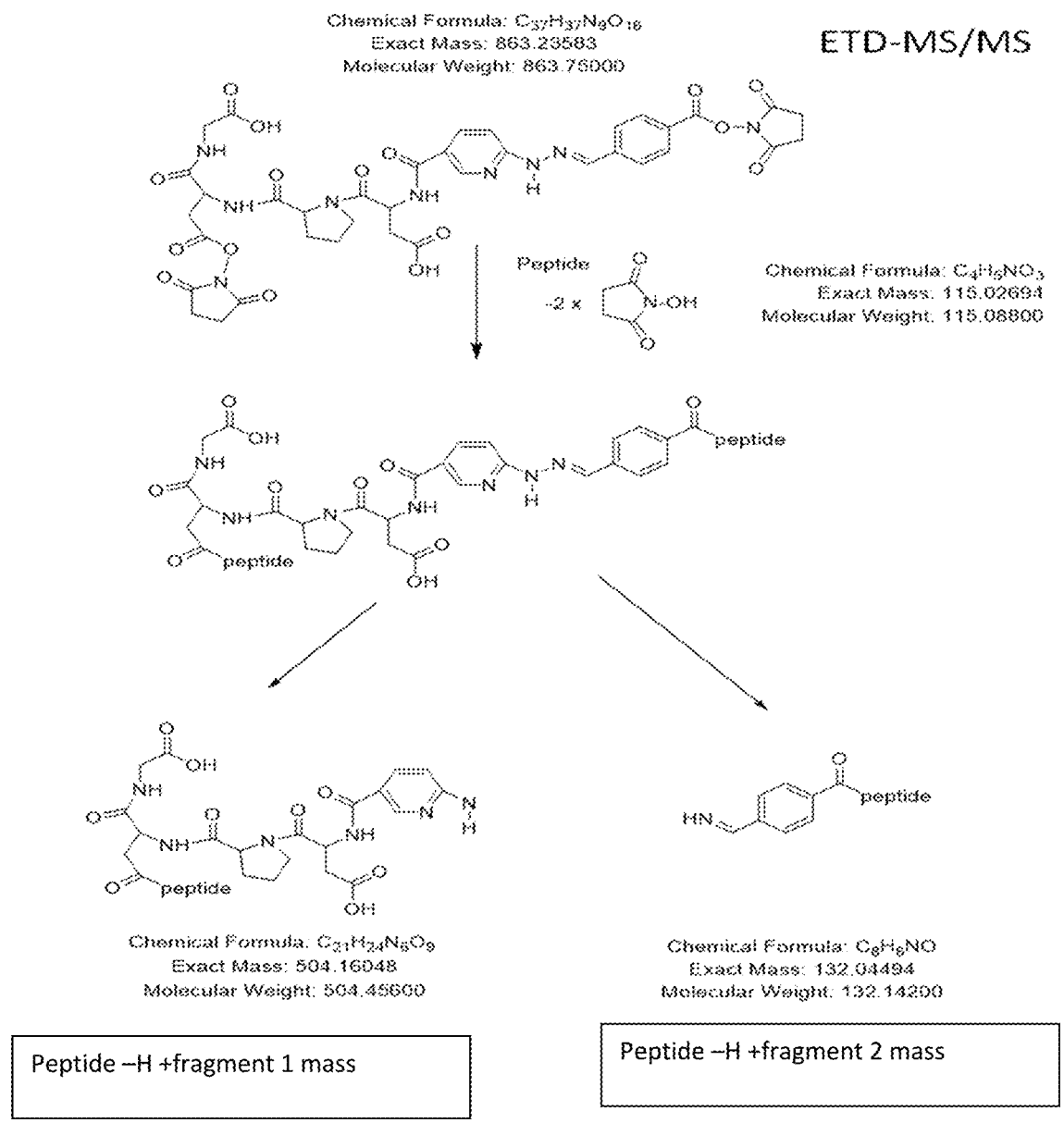
FIG. 12 illustrates the structure of DUCCT with ETD cleaved signature fragments.
Figure 13A:
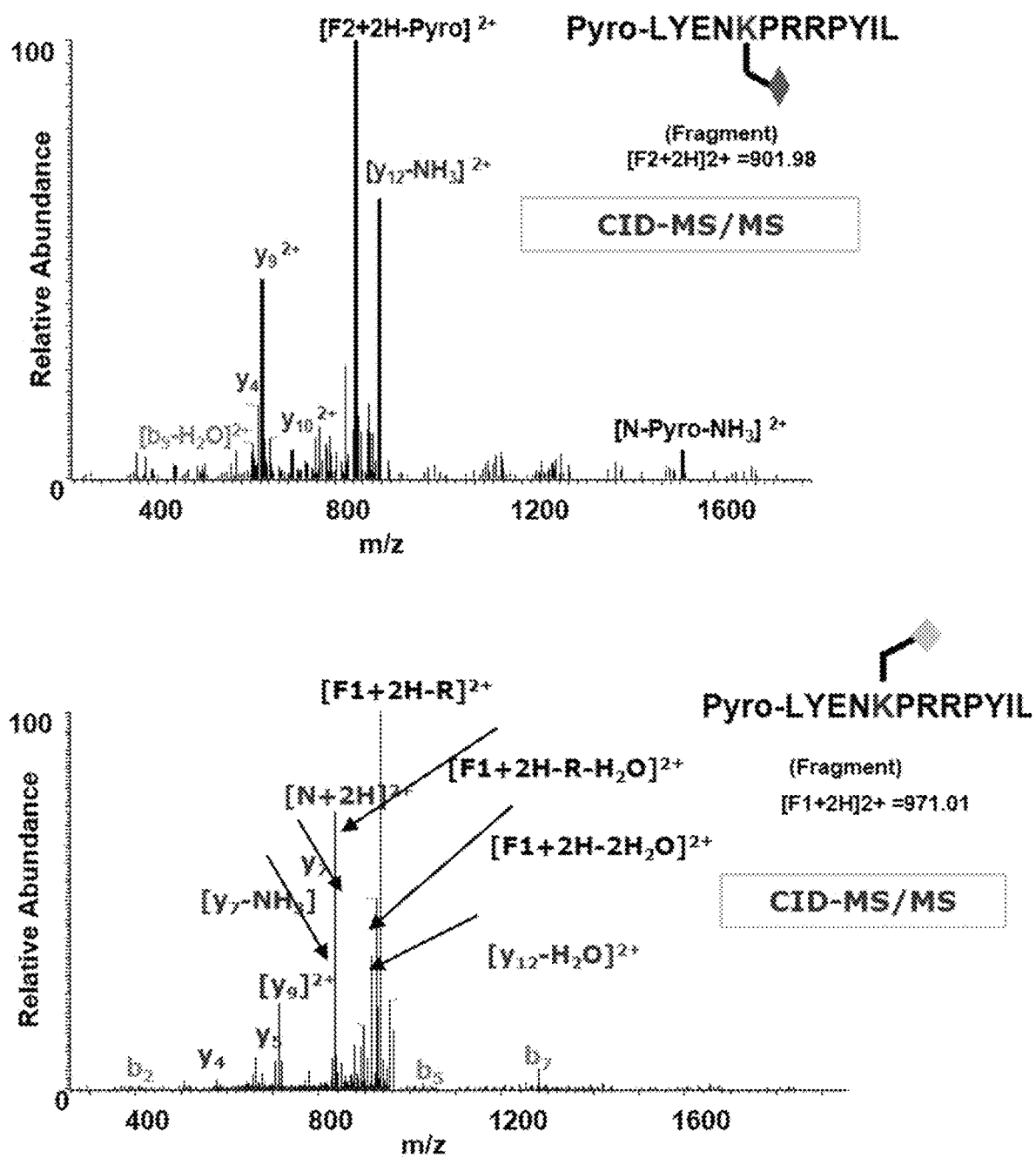
FIGS. 13A and 13B show examples of MS/MS spectra of crosslinked fragments (SEQ ID NO: 14) derived from neurotensin (FIG. 13A) and ubiquitin (SEQ ID NOs: 9 and 10; top and bottom panels, respectively) (FIG. 13B).
Figure 13B:
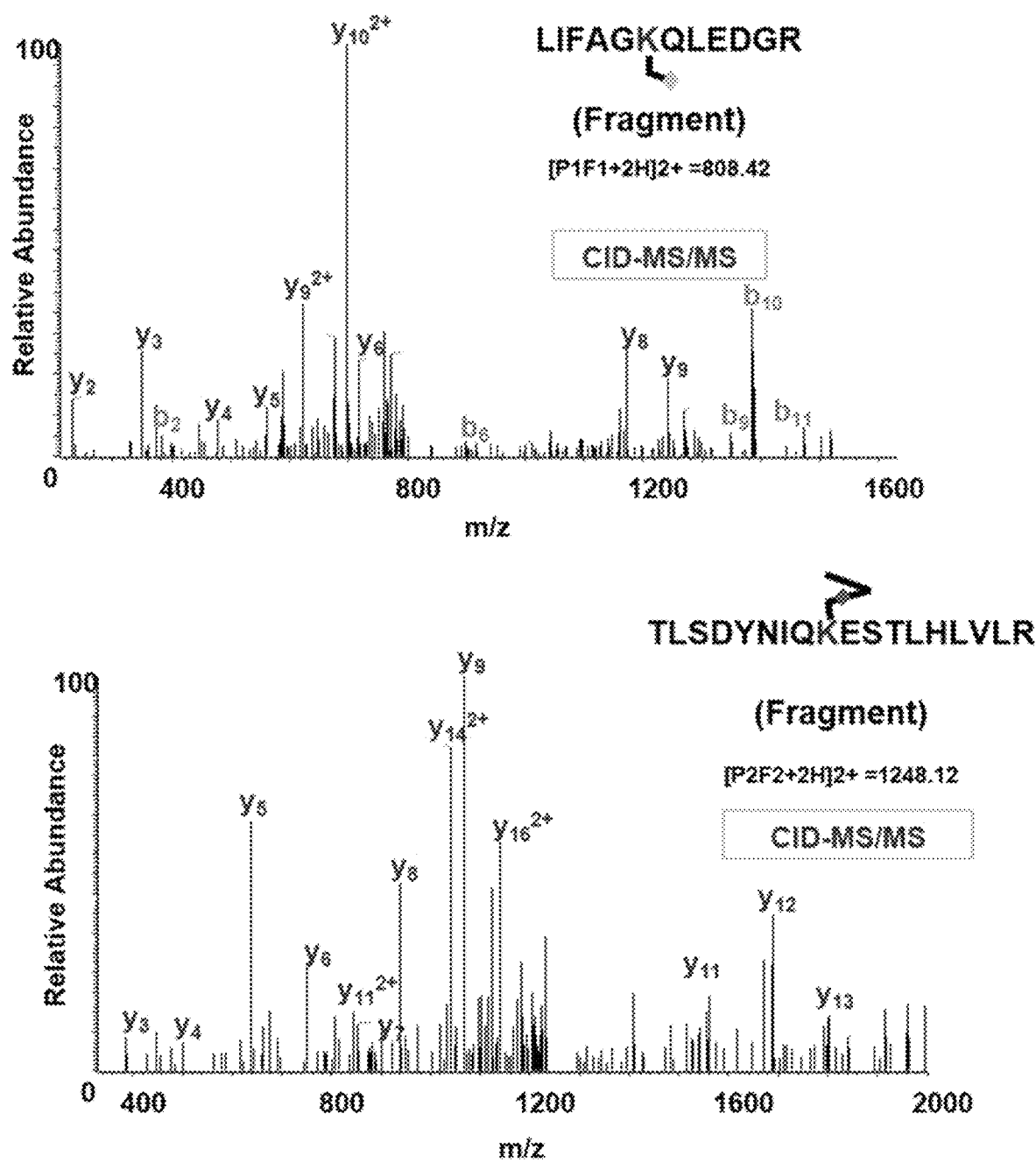

Next, the labeling efficiency of the crosslinker was tested using a small protein, ubiquitin and a large-protein BSA. Both studies showed efficient labeling with higher molecular weight dimer bands in the SDS-PAGE gel (FIG. 10). After in solution digestion and subsequent identification, few cross-linked sites in the proteins in CID and ETD MS/MS were clearly identified. Ubiquitin is a small protein, and is a suitable model protein to monitor cross-linking. The lysine 48 of ubiquitin crosslinks with lysine 63 of ubiquitin and has been reported by several groups. After crosslinking with the DUCCT cross-linker, fragmentation data were analyzed using a newly developed software tool presented herein. Even a small protein like ubiquitin can generate 30,000 scan in LC-MS/MS. Several cross-linked peptides were identified from ubiquitin and careful investigation clearly found the CID and ETD spectra of crosslinked lysine 48 and 63 (FIG. 11). Calculation of fragment mass was provided in Table 2. It is very clear that CID produced desired fragments (peptide mass+cross-linked fragment mass-H) after selective cleavage and ETD produced similar cleavages in specified sites (FIG. 12). Charge-reduced precursors also confirmed the charge states of the precursor even at low resolution mass spectrometer used for this study. This crosslinker can also be utilized with only CID/ETD cleavage to determine the structural properties of macromolecules. However, further MS/MS of fragment masses can also be used to distinguish the cross-linked peptides (FIG. 13B). For instance, the $MS^{3rd}$ of the fragments peaks also unambiguously confirmed the sequence of the peptides in ubiquitin and neurotensin (FIGS. 13A and 13B). It is worth noting that this is the first example of a selective ETD cleavable crosslinker.

TABLE 2

List of calculated masses and m/z value used to assign cross-linked products (Ubiquitin)

|  | Exact mass (2 decimal) | m/z |
|---|---|---|
| LIFAGKQLEDGR---- TLSDYNIQKESTLHLVLR (SEQ ID NO: 8) (inter-peptide cross-linked ubiquitin) | (1346.74 + 2130.15)(2 peptides) + 863.24(Cross-linker) − (114.02 × 2)(2 leaving groups) −2.00 (2 Hydrogen) = 4110.09 | 4111.09 (1+) 823.02 (5+) 686.02 (6+) |
| LIFAGKQLEDGR (SEQ ID NO: 9) (Peptide 1) + Fragment residue mass 1 (CID) | 1346.74 (peptide) + 270.11 (Fragment 1) − 1 (1 Hydrogen) = 1615.85 | 1616.85 (1+) 808.93 (2+) 539.62 (3+) 404.96 (4+) |
| TLSDYNIQKESTLHLVLR (SEQ ID NO: 10) (Peptide 2) + Fragment residue mass 2 (CID) | 2130.15 (peptide) + 365.09 (Fragment 2) − 1 (1 Hydrogen) = 2494.24 | 2495.24 (1+) 1248.12 (2+) 832.41 (3+) 624.56 (4+) |
| LIFAGKQLEDGR (SEQ ID NO: 9) (Peptide 1) + Fragment residue mass 1 (ETD) | 1346.74 (peptide) + 504.16 (Fragment 1) − 1 (1 Hydrogen) = 1849.90 | 1850.90 (1+) 925.95 (2+) 617.63 (3+) 463.48 (4+) |
| TLSDYNIQKESTLHLVLR (SEQ ID NO: 10) (Peptide 2) + Fragment residue mass 2 (ETD) | 2130.15 (peptide) + 132.04 (Fragment 2) − 1 (1 Hydrogen) = 2261.19 | 2262.19 (1+) 1131.60 (2+) 754.73 (3+) 566.30 (4+) |

Figure 14:
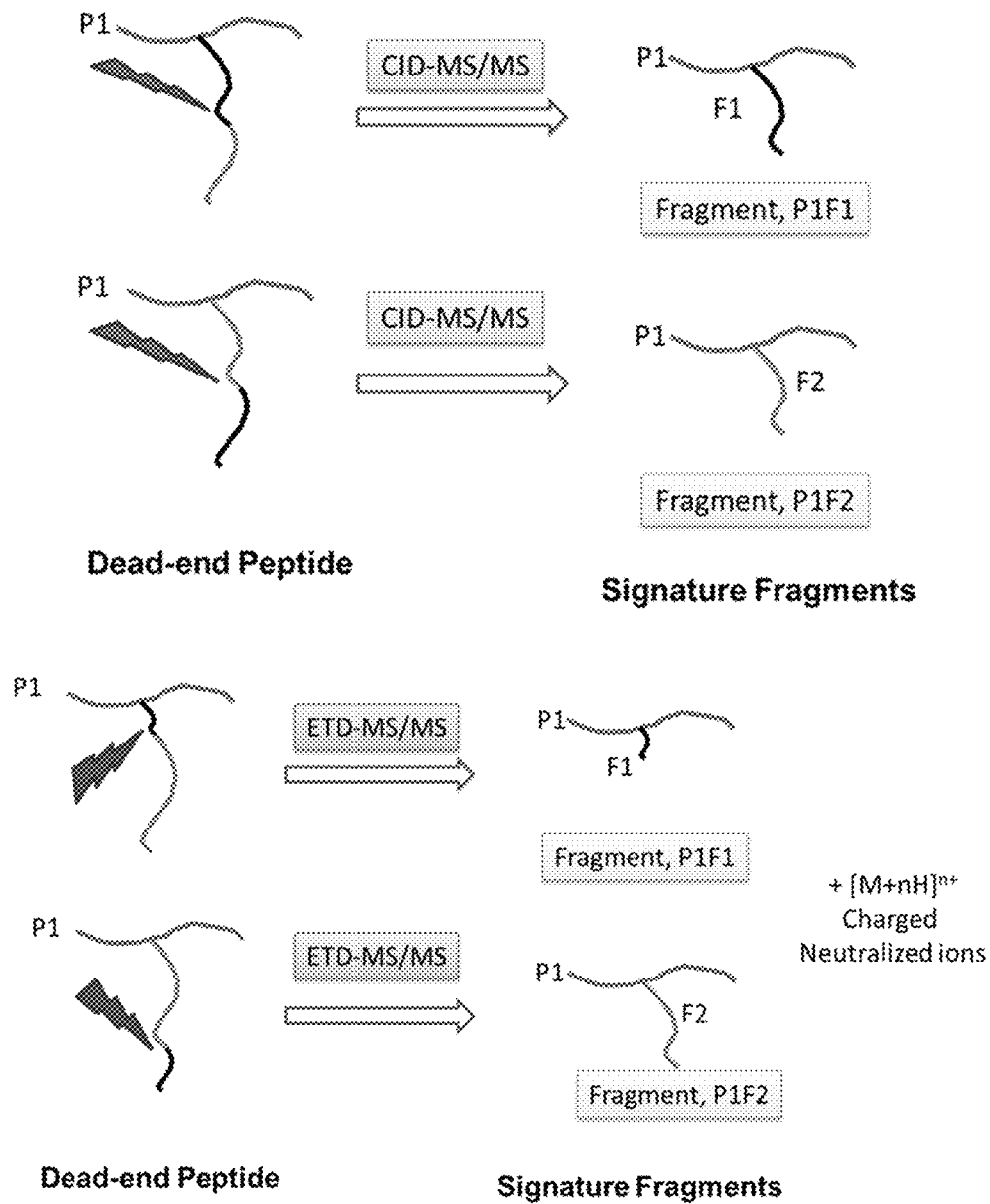
FIG. 14 illustrates CID (top panel) and ETD (bottom panel) fragmentation patterns of dead-end peptides (one-end hydrolyzed).
Figure 15A:
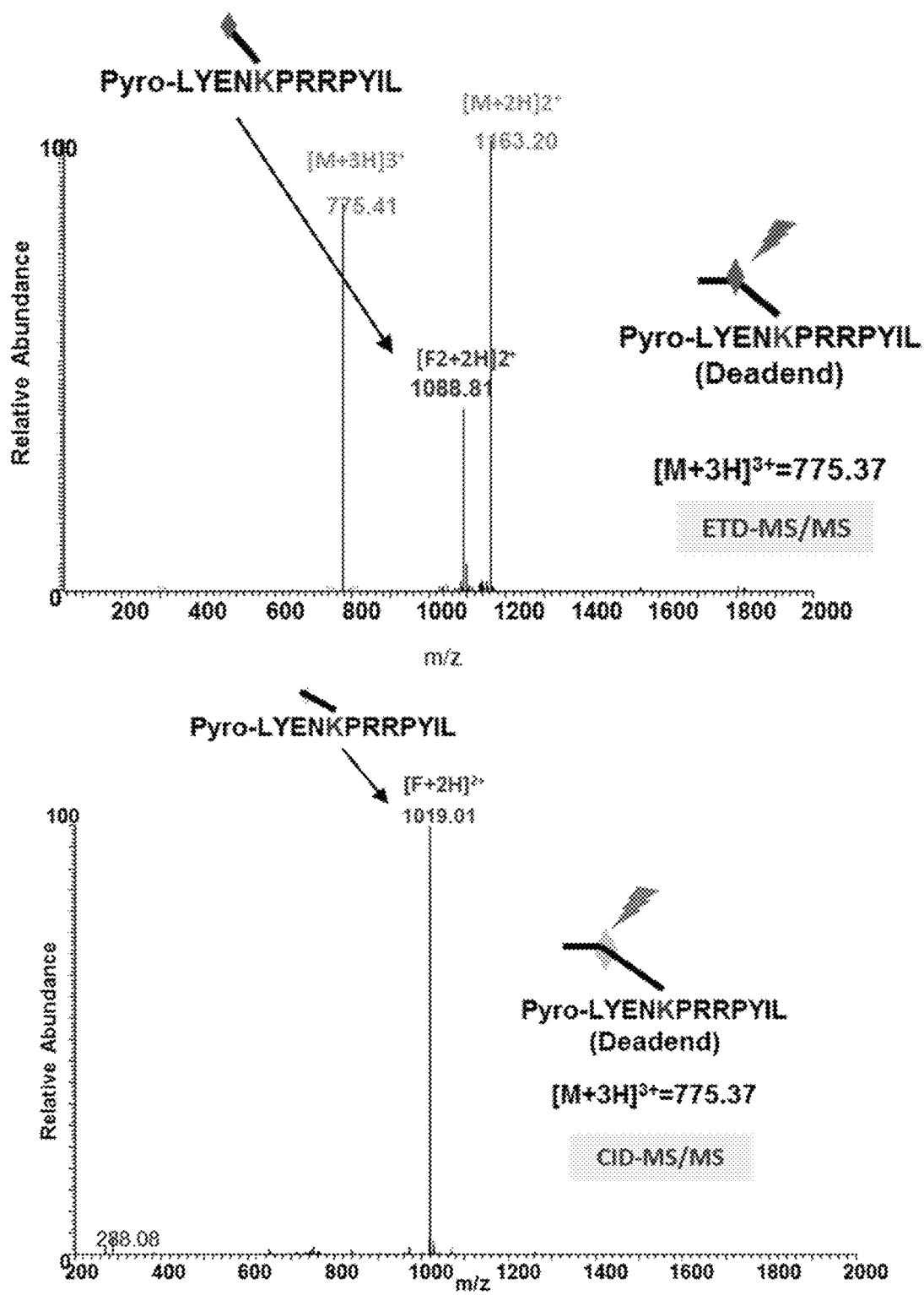
FIGS. 15A and 15B show a simplified demonstration of CID and ETD mass spectra of dead-end peptides (SEQ ID NO: 14) derived from neurotensin (SEQ ID NO: 13) (FIG. 15A) and ubiquitin (i.e., SEQ ID Nos: 9 and 12 (FIG. 15B).
Figure 15B:
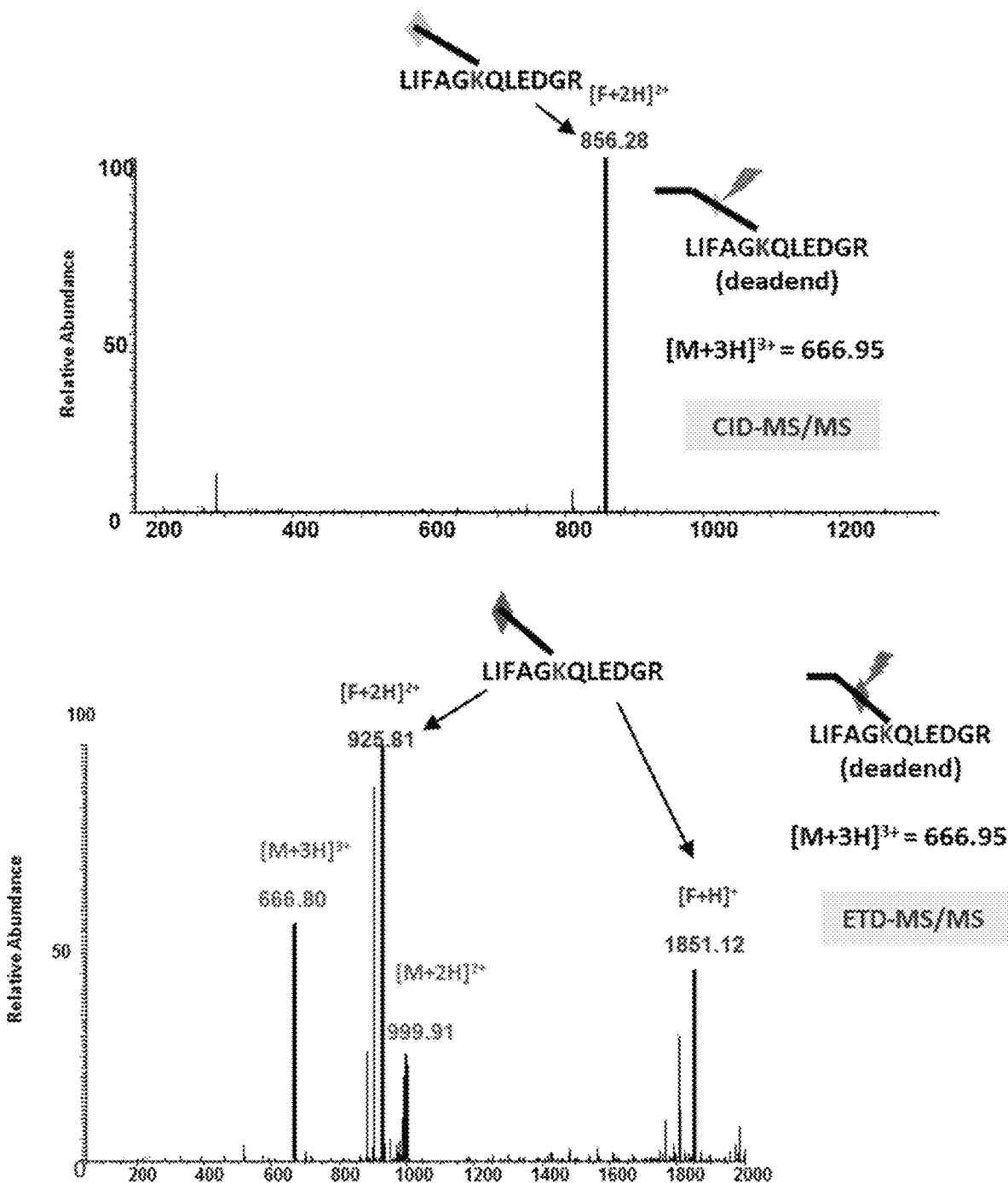
Figure 15:
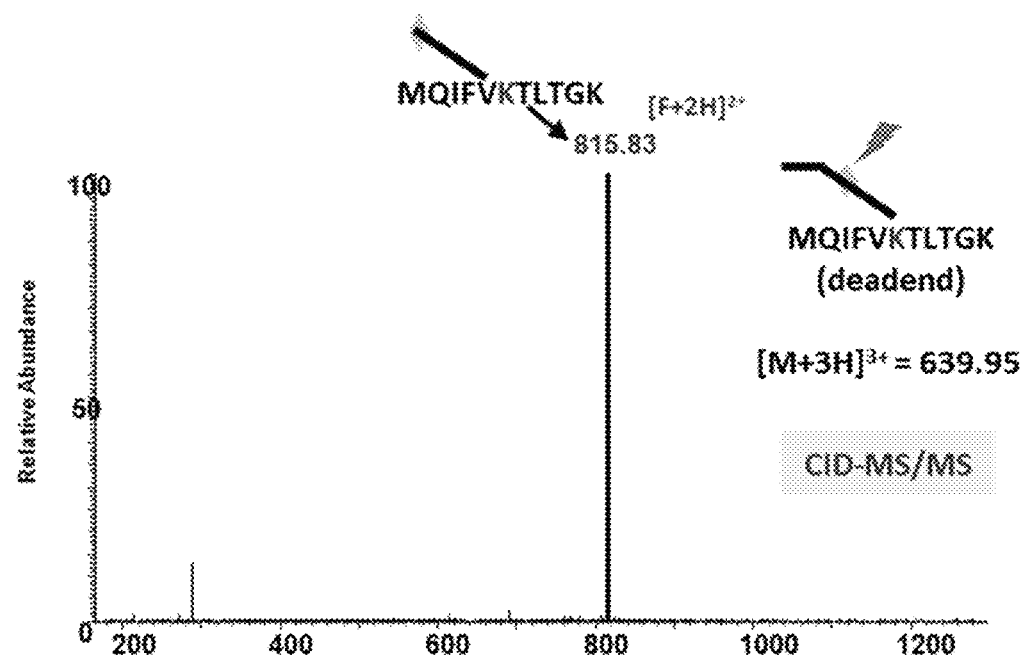
Figure 15:
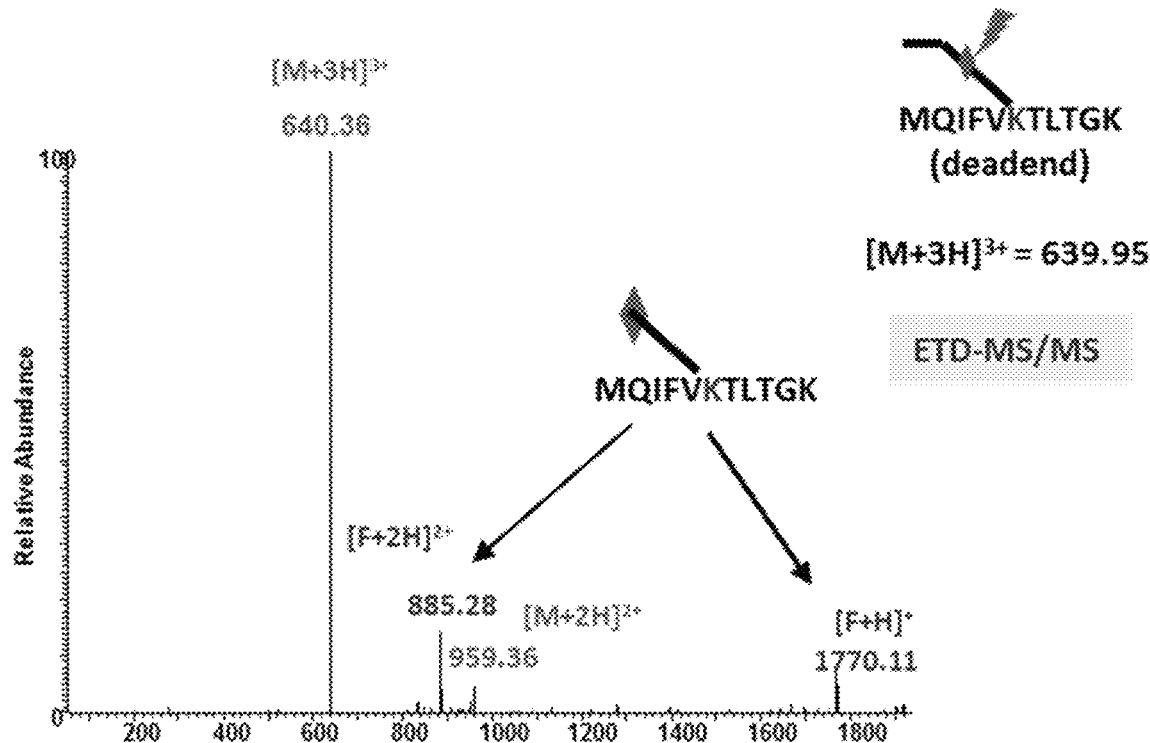

Dead-end cross-linking was identified very efficiently in the neurotensin crosslinked peptides. Dead-end peptides are a very good indicator of the surface lysines as well as reactive lysine residues. Identifying dead-end with cleavable crosslinker requires further MS/MS of cross-linked peptides due to the generation of single peptide ion in the mass spectrum. For a heterogeneous cleavable crosslinker, dead-end peptides can react in two different ways depending on the reactive groups. Majority of the mass spectra will be one peptide but some of them can be a mixture two peptides. Nonetheless, the cross-linked precursor mass database of dead-end peptides will filter them clearly at the first stage of database search. As dead-end crosslinked peptides can produce a peptide with added crosslinker masses, sometimes it can produce both peptides due to un-even fragmentation on both cleavage sites due to the labeling positions (FIG. 14). This problem can easily be solved by these dual cleavable properties in the crosslinker. Two CID and ETD MS/MS will unambiguously identify dead-end peptides. The dead-end precursor peptide was calculated and found at m/z 775 (3+) for neurotensin. After CID-MS/MS it cleaved at DP bond and generated peptide with added crosslinker masses at m/z 1019.01 (FIG. 15).

In the ubiquitin crosslinking experiments, several dead end peptides were observed. One of the dead end peptides is shown in FIG. 16. The top left-side of FIG. 16 shows the SDS-PAGE of biotin-avidin pulldown experiments, while the top, right-side shows a Venn diagram of the number of protein identified. FIG. 16 also shows a heatmap of few selected proteins identified exclusively in crosslinked samples after pulldown studies with avidin. A single peptide was identified in the mass spectrum after CID cleavage. This peptide required further MS/MS/MS for confident identifications. Due to the dual cleavable properties, further ETD MS/MS produced same peptides with added cross linker parts. Charge neutralized peaks were also observed and provided the charge states of this precursor. It is clear that CID and ETD clearly pinpointed same crosslinked peptide with high confidence.

Example 2: Confidence in Crosslinked Peptide Identifications

An automated software was also developed to analyze this data. Even simple proteins in a LC-MS/MS experiment generate 20,000 mass spectra. To test how confidently cross-linked peptides can be identified using two differential cleavages, a theoretical database of cross-linked peptides was generated using precursor and fragment masses. An mgf (contained experimental list of precursors and fragment ions masses) file of experimental LS-MS/MS experiment of crosslinked ubiquitin was also generated. Approximately 30500 mass spectra scans were found in the mgf file. Searching the mgf file with the theoretical cross-linked database identified a list of hits in the CID search. It will require further MS/MS of both cross-linked peptides to receive full confidence on the cross-linked peptides. The mgf file of ETD-MS/MS of the cross-linked ubiquitin was also searched against the theoretical database of cross-linked peptides. Several hits were identified from the theoretical ETD datasets. After comparing the common sequences identified in both datasets with precursor m/z restricted to ±0.5 Da, several peptide sequences were identified very confidently from both datasets (Table 3). It is very clear that CID and ETD information pinpointed the confidence cross-linked peptides from the experiments. Data from the MS/MS of these cleavage parts have also been shown, and confirmed the identities of some of the peptide sequence with high confidence. These three steps; 1) CID-MS/MS of cross-linked peptides, and 2) MS$^{3rd}$ of the cleaved crosslinked peptide parts, and 3) ETD-MS/MS of crosslinked peptides, can simultaneously identify the crosslinked peptides without any ambiguity. It is also worth mentioning that a high resolution mass spectrometer will significantly reduce hits due to the search threshold of precursor and fragment masses.

TABLE 3

CID and ETD together pinpointed the list of crosslinked sites in ubiquitin

| PrecursorCID | PrecursorETD | Sequence | ScanCID | Sequence Coming from | ScanETD |
|---|---|---|---|---|---|
| 618.26733 | 618.25914 | LIFAGKQLEDGR--- AKIQDKEGIPPDQQR (SEQ ID NO: 11) | scans: | both sequences coming from ubiquitin | scans: |
| 618.35066 | 618.34248 | LIFAGKQLEDGR--- AKIQDKEGIPPDQQR (SEQ ID NO: 11) | scans: | both sequences coming from ubiquitin | scans: |

TABLE 3-continued

CID and ETD together pinpointed the list of crosslinked sites in ubiquitin

| PrecursorCID | PrecursorETD | Sequence | ScanCID | Sequence Coming from | ScanETD |
|---|---|---|---|---|---|
| 650.35175 | 650.26024 | LIFAGKQLEDG R--- AKIQDKEGIPP DQQR (SEQ ID NO: 11) | scans: | both sequences coming from ubiquitin | scans: |
| 823.19098 | 823.34947 | LIFAGKQLEDG R--- AKIQDKEGIPP DQQR (SEQ ID NO: 11) | scans: | both sequences coming from ubiquitin | scans: |

Example 3—Labeling Studies in Cell Lysate

Figure 17:
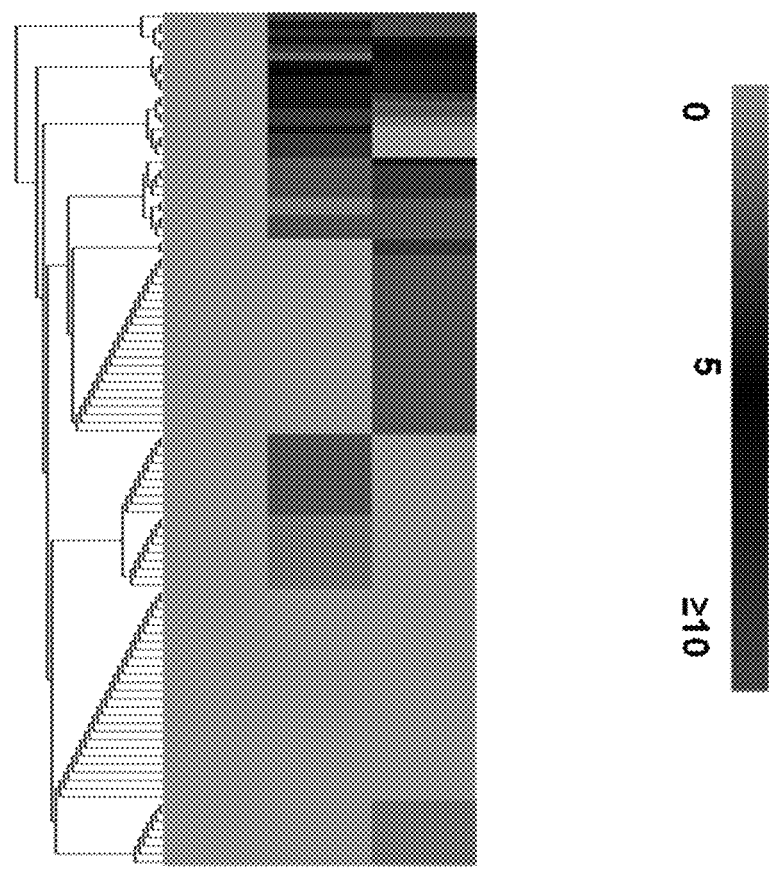
FIG. 17 shows a full heat map of proteins which were observed in BioLPS (none) but BS3 and DUCCT pulldown studies.
Figure 18:
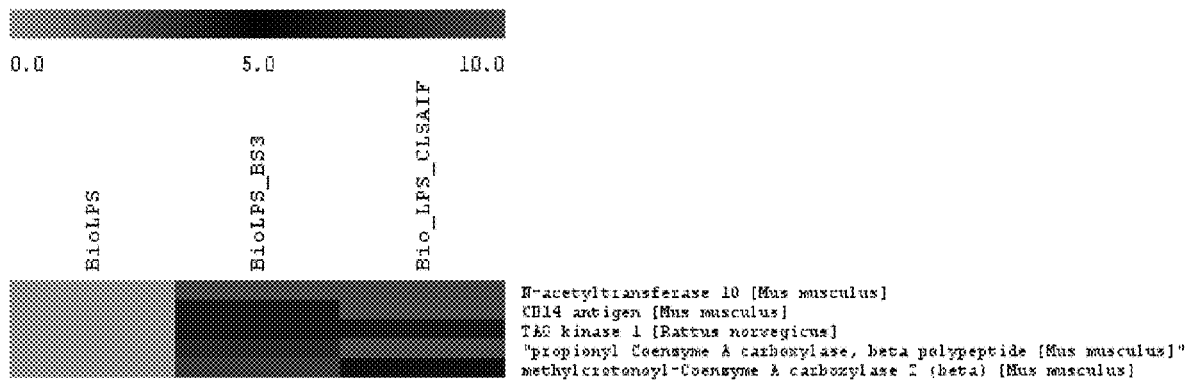
FIG. 18 shows a partial heatmap of FIG. 16 with all the proteins.

In order to determine the labeling efficiencies of the DUCCT cross-linkers in pulldown samples, the DUCCT crosslinker cross linker was tested in immune cell macrophages after stimulation with Toll-Like Receptor 4 (TLR4) ligand lipo-polysaccharides (LPS). Raw 264.7 macrophage cells were grown and treated with 1 h LPS-biotin followed by crosslinking with the DUCCT crosslinker and BS3, a commercial crosslinker. After SDS-PAGE separation of samples, in gel digestion was carried out for each gel lane (24 pieces) and LC-MS/MS experiments were performed. The DUCCT cross-linker treated sample identified more proteins compared to its BS3 counterpart (FIG. 16). After careful investigation, a few known interactors were identified for LPS-biotin treated crosslinked samples. CD14, a LPS responsive protein was identified with high spectral counts in the DUCCT crosslinker compared to BS3. No CD14 peptide was identified in the control LPS-biotin treated sample (FIGS. 16, 17, 18). These studies clearly showed that the labeling efficiencies of the DUCCT cross-linker was better than a widely used commercial crosslinker BS3.

Example 4—Synthesis of the DUCCT-Biotin-Crosslinker

A dual mass Spectrometry cleavable crosslinker was also synthesized using biotin as an enrichment reagent. This enrichment reagent-tagged DUCCT crosslinker is used to enrich cross-linked peptides from a large-scale experiment using biotin-avidin affinity chromatography (FIG. 4). Both CID and ETD cleavage sites were incorporated using the same chemistry as shown for the DUCCT crosslinker. After CID MS/MS, this biotin-labelled crosslinker it will produce efficient cleavage at DP bonds specified in FIG. 4. The predicted fragment signatures after CID-MS/MS are shown in FIG. 5. As mentioned before, ETD-MS/MS will not generate any fragmentation signature until the crosslinker is conjugated with peptides or proteins.

The cross linker was synthesized using Fmoc peptide synthesis reagents with an Applied Biosystems 431 Peptide Synthesizer at the 0.25 mmole scale. The biotin form of the cross linker was synthesized as the first by inserting lysine (biotin) between the glycine and the supersensitive aspartate residue using Fmoc lys(biotin) (Novabiochem). Fmoc Gly was first coupled to the resin followed by the supersensitive form of Fmoc Asp, Fmoc-Asp(O-2-PhiPr) or Fmoc glycine Wang resin (Anaspec. Inc) was followed by the Fmoc supersensitive Asp. This was then followed by coupling proline and then the typical form of Asp using Fmoc Asp-OtBu. The free amine of this Asp was coupled to Hydralink 6-Fmoc-HNA reagent. After Fmoc was released, 4-formylbenzoic acid was added which formed the hydrazone link and a terminal carboxylic acid. The protection group of the supersensitive asp was removed by 2% TFA in dichloromethane to create the second carboxylic acid. These two carboxylic acids were activated by DCC to which the NHS esters were then formed by adding 2 mmole N-hydroxysuccinimide (Aldrich) with the DCC. The final compound was cleaved from the resin by 95% TFA with 5% water for 1 hr. The product was precipitated with diethyl ether, centrifuged, the pellet dissolved in 0.1% TFA water and quickly lyophilized.

Figure 19:
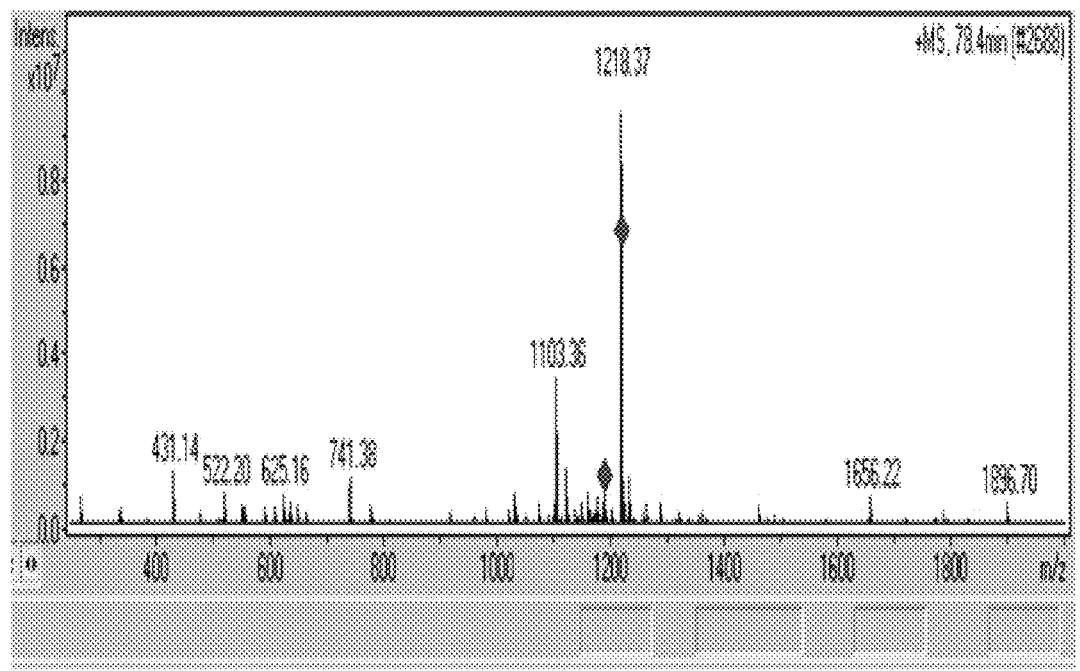
FIG. 19 shows a LC-MS experiment on DUCCT-biotin.
Figure 20:
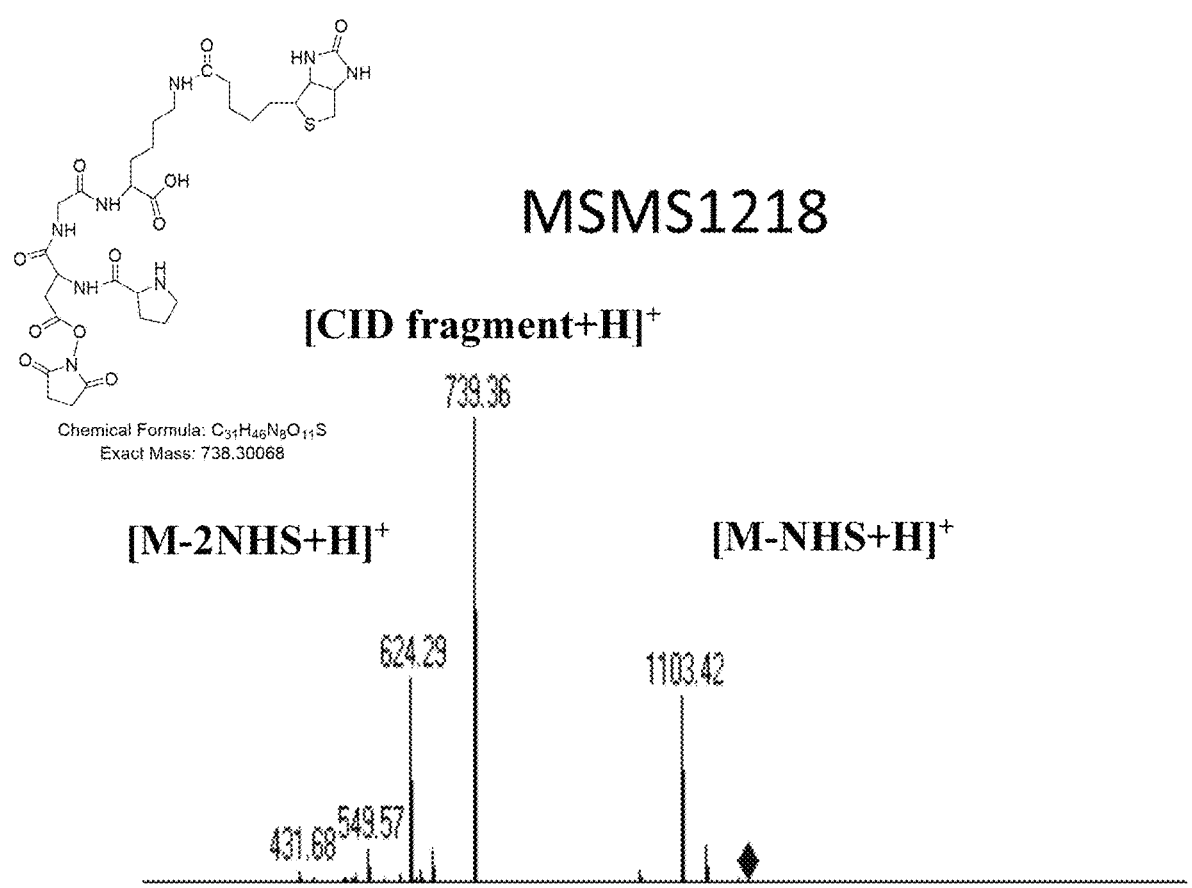
FIG. 20 shows efficient cleavage at CID-MS/MS cleavage sites of a biotinylated cross-linker.

The crosslinker was synthesized and an m/z 1218 was observed in the mass spectrum (FIG. 19). After CID-MS/MS, cleavage at the CID site was clearly shown by the presence of a fragment at m/z 739.36, which corresponds to the mass of [CID fragment+H+]. Two other peaks were observed at m/z 1103.42 and 624.29 which correspond to the loss of two NHS groups (FIG. 20). These two peaks will not be observed after covalent attachment to proteins or peptides due to their functions as leaving groups.

In order to efficiently enrich cross-linked peptides and reduce mass spectral interference from the biotin conjugated compound, the DUCCT-biotin crosslinker can be synthesized as a photo-cleavable DUCCT crosslinker (PC-DUCCT-biotin). The crosslinker will be released from the biotinylated part after UV-light exposures and will release the cross-linked peptides from avidin beads used to capture the biotinylated DUCCT crosslinker. Subsequent CID and ETD MS/MS will generate signature mass spectra for identification of cross-linked peptides. The CID and ETD-MS/MS will identify the cross-linked peptides according to the DUCCT and DUCCT-biotin crosslinker as previously mentioned.

In FIG. 6, the red line denotes the photo-cleavage site after UV light exposures. After reaction with protein or peptides, the cross-linked peptide will be enriched using biotin-avidin affinity chromatography. The cross-linked peptides or protein can be eluted from the avidin bead and subsequent UV light exposure will release the biotinylated part of the compound and cross-linked portion will be attached to the peptides.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the devices are not intended to be limited to the particular forms disclosed. Rather, they include all modifications and alternatives falling within the scope of the claims, and embodiments other than the one shown may include some or all of the features of the depicted embodiment. For example, components may be omitted or combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A method for mapping protein-protein interactions of a protein complex, the method comprising:

contacting a cross-linker with the protein complex under conditions in which two or more reactive groups in the cross-linker react with a reactive group in the protein complex to form a cross-linked protein complex;

digesting the protein complex with an enzyme to form peptides and/or peptide fragments; and using mass spectrometry ($MS^Z$) to identify the protein and/or peptide fragments, wherein Z is an integer between 1 and 4, inclusive, wherein the cross-linker comprising at least two reactive groups, and at least a first cleavage site and a second cleavage site, wherein the cross-linker has the formula:

Formula I

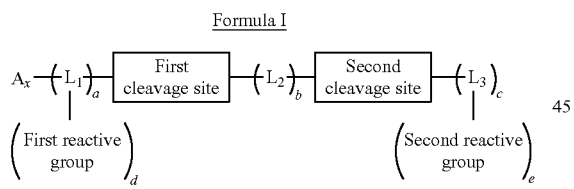

wherein:

a, b, and c are independently integers between 0 and 20, inclusive, with the proviso that a and b are each at least 1;

d and e are independently integers between 1 and 20, inclusive;

the first cleavage site and the second cleavage site are independently amide bonds, nitrogen-nitrogen hydrazone bond, mono-oxidized thioether bonds, urea-based, nitrogen-carbon bonds vicinal to an amide bond, or a C—Cα bond in peptides; wherein at least one cleavage site contains a nitrogen-nitrogen hydrazone bond, each occurrence of $L_1$, $L_2$, and $L_3$ is independently an amino acid, —C(O)-unsubstituted heteroaryl-, —C(O)-substituted heteroaryl-, -unsubstituted aryl-(CO)—, -substituted aryl-(CO)—, —C(O)NH—, —C(O)NR'—, —NR'C(O)—, —C(O)O—, —OC(O)—, —C(O)OCH$_2$—, —SO$_2$NR'—, —CH$_2$R'—, —O—, —NR'H—, —NR'—, —OCONH—, —NHCOO—, —OCONR'—, —NR'COO—, —NHCONH—, —NR'CONH—, —NHCONR'—, —NR'CONR'—, —CHOH—, —CR'OH—, unsubstituted alkyl, substituted alkyl, unsubstituted alkylene, substituted alkylene, substituted alkenyl, unsubstituted alkenyl, substituted alkylamino, unsubstituted alkylamino, substituted carbonyl, unsubstituted carbonyl; an affinity group, or a combination thereof; and R' is hydrogen, halogen, hydroxyl, unsubstituted alkyl, substituted alkylene, unsubstituted alkylene, substituted alkenyl, unsubstituted alkenyl, substituted alkylamino, unsubstituted alkylamino, substituted carbonyl, unsubstituted carbonyl, an aryl group, or a heterocyclic group; and $A_x$ is independently one or more amino acids, —C(O)—(CH$_2$)$_n$—O-substituted aryl-substituted alkyl-, —C(O)—(CH$_2$)$_n$—O-unsubstituted aryl-substituted alkyl-, —C(O)—(CH$_2$)$_n$—O-substituted heteroaryl-substituted alkyl-, —C(O)—(CH$_2$)$_n$—O-unsubstituted heteroaryl-substituted alkyl-, —C(O)—(CH$_2$)$_n$—, —C(O)NH—, —C(O)NR'—, —NR'C(O)—, —C(O)O—, —OC(O)—, —C(O)OCH$_2$—, —SO$_2$NR'—, —CH$_2$R'—, —O—, —NR'H—, —NR'—, —OCONH—, —NHCOO—, —OCONR'—, —NR'COO—, —NHCONH—, —NR'CONH—, —NHCONR'—, —NR'CONR'—, —CHOH—, —CR'OH—, unsubstituted alkyl, substituted alkyl, unsubstituted alkylene, substituted alkylene, substituted alkenyl, unsubstituted alkenyl, substituted alkylamino, unsubstituted alkylamino, substituted carbonyl, unsubstituted carbonyl, an affinity group, or a combination thereof, wherein n is an integer between 1 and 10, inclusive; R' is hydrogen, halogen, hydroxyl, unsubstituted alkyl, substituted alkyl, substituted alkylene, unsubstituted alkylene, substituted alkenyl, unsubstituted alkenyl, substituted alkylamino, unsubstituted alkylamino, substituted carbonyl, or unsubstituted carbonyl, wherein the first cleavage site and the second cleavage site are differentially cleaved by two different mass spectrometric techniques, and wherein the first cleavage site and second cleavage site are located in a spacer or linker region of the cross-linker between at least two reactive groups.

2. The method of claim 1, wherein the enzyme is a trypsin.

3. The method of claim 1, wherein:
(a) the through-space distance between at least two reactive groups is between 9 Å and 25 Å, inclusive, 9 Å and 18 Å, inclusive, 9 Å and 13 Å, inclusive, or between 11 Å and 12 Å, inclusive;
(b) the two different mass spectrometric techniques are selected from the group consisting of collision induced dissociation (CID), electron transfer dissociation (ETD), and electron capture dissociation (ECD); or
(c) the reactive groups are the same or different.

4. The method of claim 3, wherein each occurrence of a first reactive group and a second reactive group is independently N-hydroxysuccinimide ester, sulfo-N-hydroxysuccinimide ester, maleimide, sulfydryl, hydroxyl, amine, azide, glycidyl, aldehyde, diazirine, diazoacetate ester, acrylate, nitrophenyl ester, nitrile, or a combination thereof.

5. The method of claim 1, wherein the first cleavage site comprises

Pro-X                         Formula II wherein, Pro is proline, and X is aspartate.

6. The method of claim 1, wherein the second cleavage site comprises a nitrogen-nitrogen hydrazone bond.

7. The method of claim 1, having wherein the cross-linker has the formula:

Formula III.

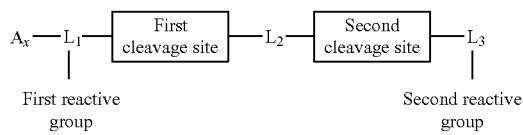

8. The method of claim 1, wherein;
$L_1$ is aspartate; $A_x$ is selected from the group consisting of one or more amino acids, —C(O)—$(CH_2)_n$—, and an affinity group.

9. The method of claim 1, wherein; the first cleavage site is Pro-Asp; $L_2$ is —C(O)-unsubstituted heteroaryl-, or —C(O)-substituted heteroaryl; the second cleavage site is a nitrogen-nitrogen hydrazone bond;

$L_3$ is -unsubstituted aryl-C(O)—, or substituted aryl-C(O)—; and/or the first reactive group and second reactive group are N-hydroxysuccimide ester.

10. The method of claim 1, wherein $A_x$ is selected from the group consisting of glycine, —C(O)—$(CH_2)_n$—O-substituted aryl-substituted alkyl-, —C(O)—$(CH_2)_n$—O-unsubstituted aryl-substituted alkyl-, —C(O)—$(CH_2)_n$—O-substituted heteroaryl-substituted alkyl-, —C(O)—$(CH_2)_n$—O-unsubstituted heteroaryl-substituted alkyl-, —C(O)—$(CH_2)_n$—, an affinity group, or a combination thereof.

11. The method of claim 10, wherein n is 3, 4, or a combination thereof.

12. The method of claim 11, wherein the one or more amino acids are selected from the group consisting of glycine, glutamate, and lysine.

13. The method of claim 8, wherein n is 4.

14. The method of claim 13, wherein the one or more amino acids are selected from the group consisting of glycine and lysine.

15. The method of claim 1, wherein the affinity group is selected from the group consisting of biotin, hemagglutinin, streptavidin, fusion protein, purification tags, antibodies or antigen-binding fragment thereof, an RNA or protein shaped to specifically interact with a target, a small molecule or element with specific binding affinity, or a ligand for a cell, a cell-surface receptor, or cell-surface antigen.

16. The method of claim 1, wherein the cross-linker has a CID cleavable site and an ETD cleavable site.

17. The method of claim 1, wherein the cross-linker has the formula:

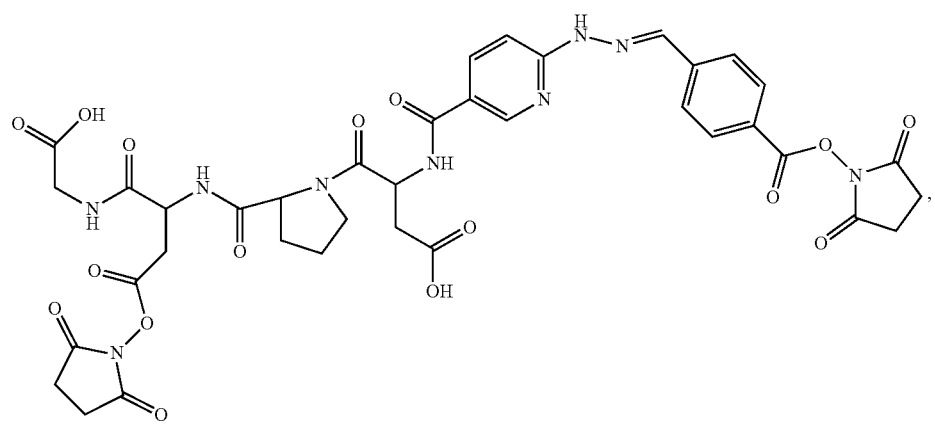

-continued
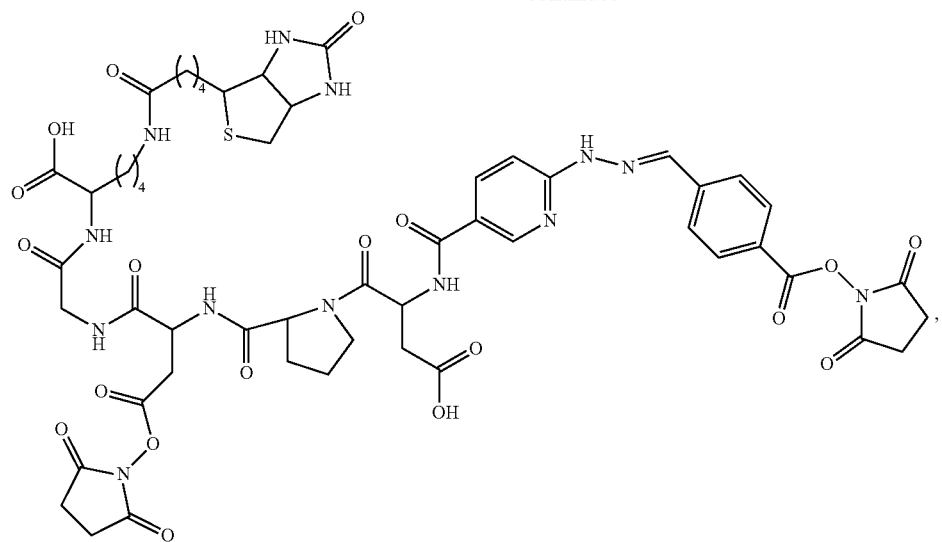
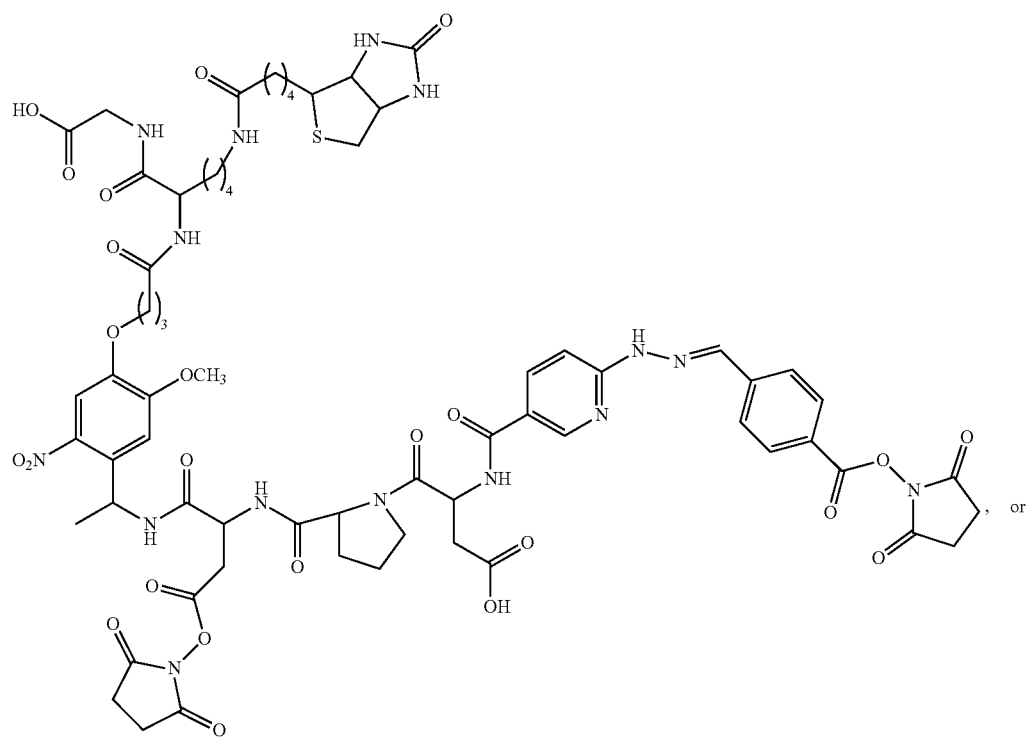
, or

-continued

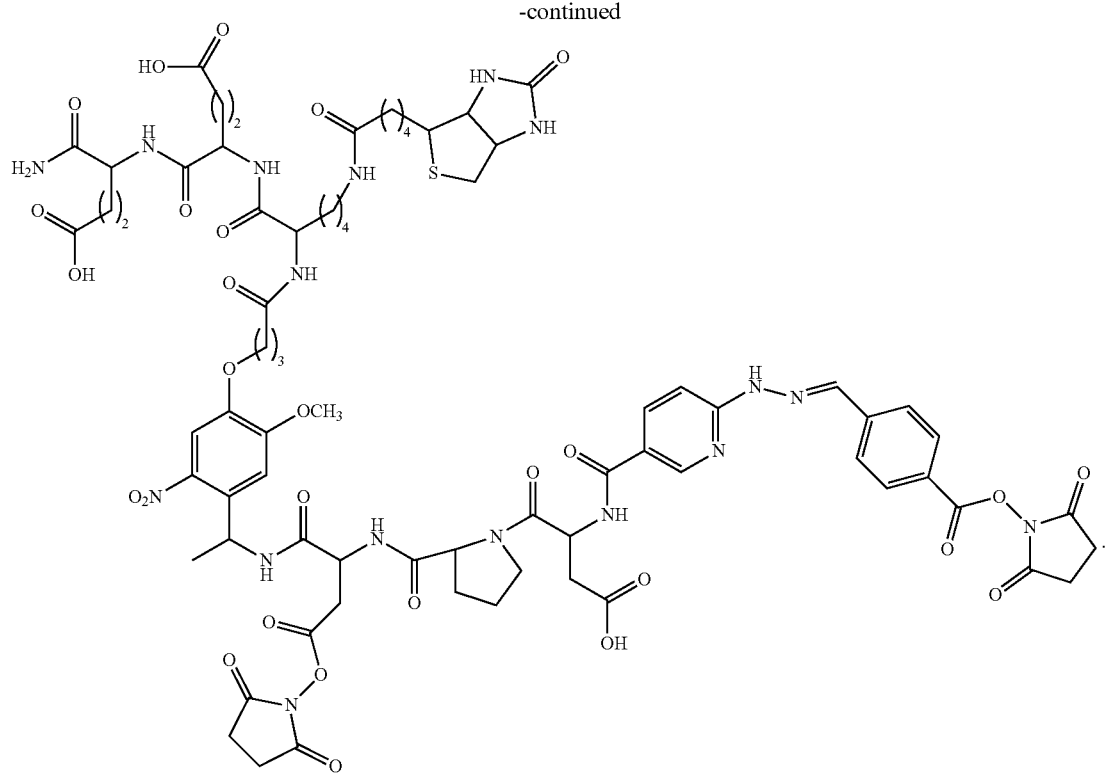

18. The method of claim 1, wherein at least one of the reactive groups binds to a macromolecule or a complex comprising a macromolecule, wherein the macromolecule or complex comprising the macromolecule is selected from the group consisting of receptor/ligand complex; biotin avidin complex, peptide/S ribonuclease complex, digoxigenin/anti-digoxigenin antibody complex, complimentary oligonucleotide pair complex and antibody/ligand complex.

19. The method of claim 1, wherein the cross-linker comprises a detectable moiety linked to a photoreactive moiety, wherein the photoreactive moiety comprises at least one group covalently bound to a substrate to form a conjugate that can be selectively photocleaved to release said substrate, wherein said substrate is selected from proteins, peptides, amino acids, lipids, cells, virus particles, fatty acids, polysaccharides and inorganic molecules.

* * * * *

SEQUENCE LISTING

```
<160> NUMBER OF SEQ ID NOS: 14

<210> SEQ ID NO 1
<211> LENGTH: 6
<212> TYPE: PRT
<213> ORGANISM: artificial sequence
<220> FEATURE:
<223> OTHER INFORMATION: Synthetic peptide

<400> SEQUENCE: 1

Tyr Pro Tyr Asp Val Pro
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Tyr Pro Tyr Asp Val Pro Asp Tyr Ala
1               5

<210> SEQ ID NO 3
<211> LENGTH: 13
<212> TYPE: PRT
<213> ORGANISM: Artificial Sequence
<220> FEATURE:
<223> OTHER INFORMATION: Synthetic peptide

<400> SEQUENCE: 3

Gly Ala Pro Val Pro Tyr Pro Asp Pro Leu Glu Pro Arg
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide

<400> SEQUENCE: 4

Gly Leu Asn Asp Ile Phe Glu Ala Gln Lys Ile Glu Trp His Glu
1               5                   10                  15
```

```
<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 5

Glu Glu Glu Glu Glu Glu
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Cys Cys Pro Gly Cys Cys
1               5

<210> SEQ ID NO 7
<211> LENGTH: 24
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Linked to PYR
<220> FEATURE:
<221> NAME/KEY: MISC_FEATURE
<222> LOCATION: (5)..(5)
<223> OTHER INFORMATION: Linked to PYR-LYENKPRRPYIL at residue K

<400> SEQUENCE: 7

Leu Tyr Glu Asn Lys Pro Arg Arg Pro Tyr Ile Leu Leu Tyr Glu Asn
1               5                   10                  15

Lys Pro Arg Arg Pro Tyr Ile Leu
            20

<210> SEQ ID NO 8
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Crosslinked to TLSDYNIQ KESTLHLVLR at residue E

<400> SEQUENCE: 8

Leu Ile Phe Ala Gly Lys Gln Leu Glu Asp Gly Arg Thr Leu Ser Asp
1               5                   10                  15

Tyr Asn Ile Gln Lys Glu Ser Thr Leu His Leu Val Leu Arg
            20                  25                  30

<210> SEQ ID NO 9
<211> LENGTH: 12
<212> TYPE: PRT
<213> ORGANISM: Artificial Sequence
<220> FEATURE:
<223> OTHER INFORMATION: Synthetic sequence
```

```
<400> SEQUENCE: 9

Leu Ile Phe Ala Gly Lys Gln Leu Glu Asp Gly Arg
1               5                   10

<210> SEQ ID NO 10
<211> LENGTH: 18
<212> TYPE: PRT
<213> ORGANISM: Artificial Sequence
<220> FEATURE:
<223> OTHER INFORMATION: Synthetic peptide

<400> SEQUENCE: 10

Thr Leu Ser Asp Tyr Asn Ile Gln Lys Glu Ser Thr Leu His Leu Val
1               5                   10                  15

Leu Arg

<210> SEQ ID NO 11
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Linked to AKIQDKEG IPPDQQR

<400> SEQUENCE: 11

Leu Ile Phe Ala Gly Lys Gln Leu Glu Asp Gly Arg Ala Lys Ile Gln
1               5                   10                  15

Asp Lys Glu Gly Ile Pro Pro Asp Gln Gln Arg
            20                  25

<210> SEQ ID NO 12
<211> LENGTH: 11
<212> TYPE: PRT
<213> ORGANISM: Artificial sequence
<220> FEATURE:
<223> OTHER INFORMATION: SYnthetic peptide
<220> FEATURE:
<221> NAME/KEY: MISC_FEATURE
<222> LOCATION: (1)..(1)
<223> OTHER INFORMATION: Linked to PYR
<220> FEATURE:
<221> NAME/KEY: MISC_FEATURE
<222> LOCATION: (5)..(5)
<223> OTHER INFORMATION: Corsslinked to PYR-LYENKPRRPYIL  at K residue

<400> SEQUENCE: 12

Met Gln Ile Phe Val Lys Thr Leu Thr Gly Lys
1               5                   10

<210> SEQ ID NO 13
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Linked to PYR

<400> SEQUENCE: 13

Leu Tyr Glu Asn Lys Pro Arg Arg Pro Tyr Ile Leu
1               5                   10
```

```
<210> SEQ ID NO 14
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Linked to PYR
<220> FEATURE:
<221> NAME/KEY: MISC_FEATURE
<222> LOCATION: (5)..(5)
<223> OTHER INFORMATION: Linked to a crosslinker fragment

<400> SEQUENCE: 14

Leu Tyr Glu Asn Lys Pro Arg Arg Pro Tyr Ile Leu
1               5                   10
```